US006528058B1

(12) United States Patent
Edgar et al.

(10) Patent No.: US 6,528,058 B1
(45) Date of Patent: Mar. 4, 2003

(54) SAPONIN ADJUVANT COMPOSITION

(75) Inventors: John Alexander Edgar, Victoria (AU); Khin Aye Tahan, Victoria (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/555,237

(22) PCT Filed: Nov. 30, 1998

(86) PCT No.: PCT/AU98/00900
§ 371 (c)(1),
(2), (4) Date: Feb. 3, 2001

(87) PCT Pub. No.: WO99/27959
PCT Pub. Date: Jun. 10, 1999

(30) Foreign Application Priority Data

Nov. 28, 1997 (AU) ............................................. PP0600

(51) Int. Cl.⁷ ......................... A61K 39/00; A61K 39/39
(52) U.S. Cl. ............................... 424/184.1; 424/278.1; 424/280.1; 424/283.1; 514/25; 514/26; 514/33
(58) Field of Search ........................... 424/184.1, 278.1, 424/280.1, 283.1; 514/25, 26, 33

(56) References Cited

U.S. PATENT DOCUMENTS 5,688,772 A    11/1997    Estrada et al. ................. 514/25

FOREIGN PATENT DOCUMENTS

| EP | 242205 A2 | 10/1987 |
| WO | WO 88/07547 | 10/1988 |
| WO | WO 91/04052 | 4/1991 |

OTHER PUBLICATIONS

Estuningsih SE, Evaluation of Antigens of Fasciola gigantica as Vaccine Against Tropical Fasciolosis in Cattle, Int. J. Parasitol, Nov. 1997, 27(11), 1419–28. Entire document.
Medline Abstract Accession No. 85301845, Vanselow BA, Vet. Rec. Jul. 13, 1985, 117 (2), 37–43. Entire document.
Medline Abstract Accession No. 92348094, East IJ, Int. J. Parasitol, May 1992, 22(3), 309–14. Entire document.

*Primary Examiner*—David Saunders
(74) *Attorney, Agent, or Firm*—Pillsbury Winthrop LLP

(57) ABSTRACT

Art adjuvant composition for stimulating an effective immune resposne to an antigenic substance when co-administered to an animal with said antigenic substance, comprising: (a) a saponin with immune stimulating activity; (b) a polycationic polyelectrolyte with immune stimulating activity; and (c) an immunoadjuvant oil.

17 Claims, 7 Drawing Sheets

US 6,528,058 B1

SAPONIN ADJUVANT COMPOSITION

Figure 1:
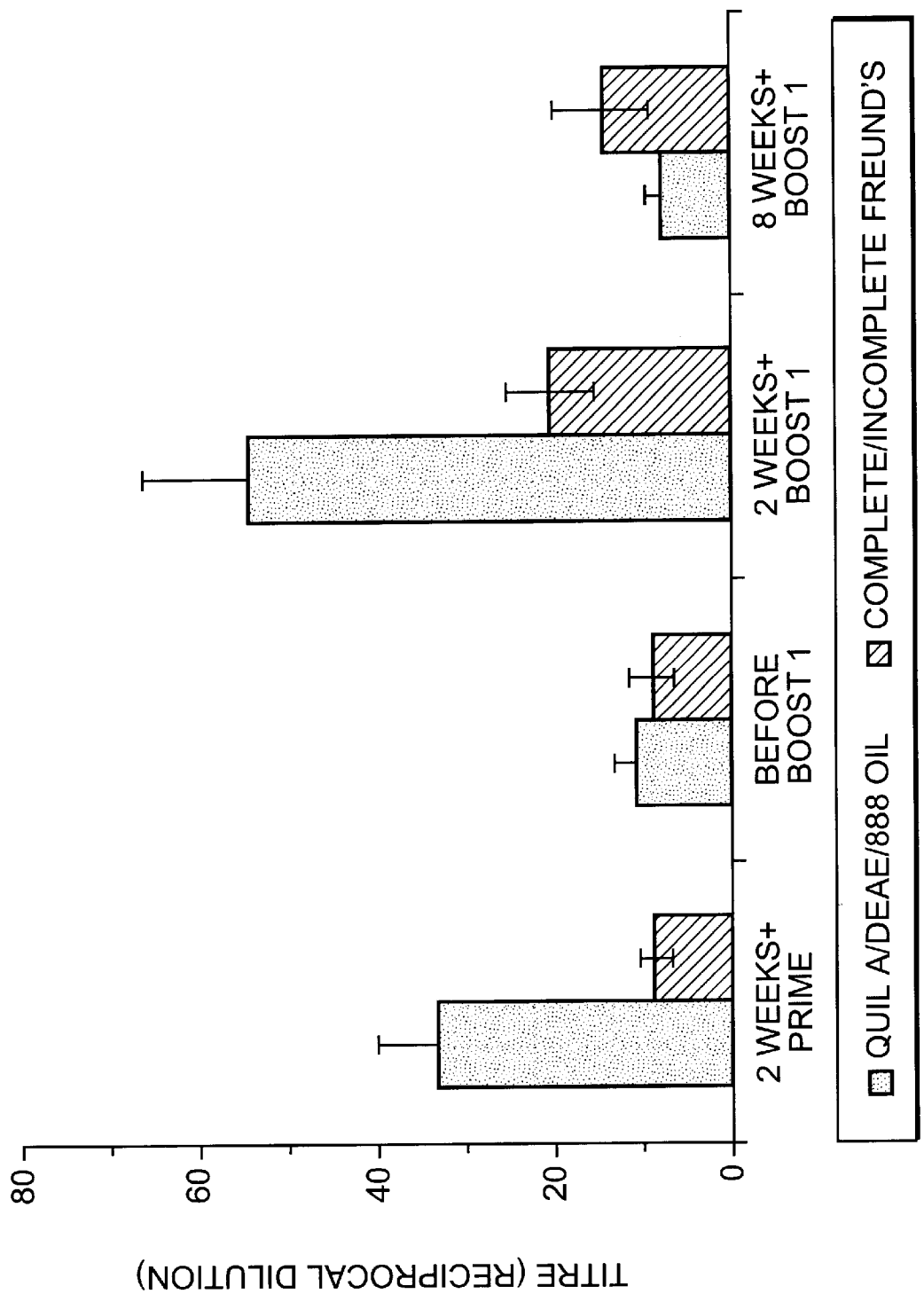

This application is the national phase of international application PCT/AU98/00990, filed Nov. 30, 1998, which designated the U.S. and which is incorporated herein by reference.

TECHNICAL FIELD

This invention relates to adjuvant compositions for stimulating an immune response to an antigenic substance when co-administered to an animal with said antigenic substance, and to vaccines containing said adjuvant composition.

BACKGROUND ART

Vaccination against disease has a long history. In general terms the technique involves injection of an antigenic substance, or antigen, into an animal whereby the presence of the antigenic substance generates an immune response in the animal. Classical vaccination techniques involve the injection of killed organisms but more recently vaccines comprising attenuated live organisms or antigenic components of an organism have been developed. It is frequently found with killed vaccines and, more particularly, with vaccines comprising a component of an organism that the immune response is substantially less than the response to natural infection. However, the effectiveness of such vaccines can be considerably enhanced by the co-administration of a suitable adjuvant composition with the antigenic substance. Adjuvants, while not necessarily being antigenic themselves, potentiate or enhance an animal's immune response to the antigenic substance with which it is challenged. There are many adjuvants known and used but there is an ongoing need to identify new and effective adjuvants which are inexpensive, which produce minimal injection site irritation and discomfort and which are widely applicable and effective.

A common formulation for vaccines is to present the antigen(s) in an aluminium hydroxide gel. While this is effective in some cases and is reasonably benign, in many cases this adjuvant fails to induce a sufficiently protective response. It is also well known that antigens emulsified in a mineral oil vehicle together with whole mycobacterial cells (Freund's complete adjuvant, FCA) can produce a generally effective immune response against a wide range of antigens. However, this formulation is unacceptable for routine use because of the inflammation, granulomas, ulceration and other lesions which can be formed at the injection site. Mineral oils alone (frequently referred to as Freund's Incomplete Adjuvant, FIA or Incomplete Freund's, ICF) are less damaging but are also less effective. Neutral oils (such as miglyol) and vegetable oils (such as arachis oil), ISCOMS and liposomes have also been used. Also effective are adjuvants containing purified mycobacterial component such as N-acetylmuramyl-L-alanyl-D-isogulutamine (MDP) or its analogues in aqueous or oil formulations. Among other adjuvants which have been or are currently used are the saponins, particularly triterpenoid mixtures such as Quil A (a purified extract from the bark of the tree Quillaja saponarioa) in aqueous solution or in the form of a matrix with cholesterol. Polycations such as diethylaminoethyldextran (DEAE dextran) can also be effective as adjuvants in some cases.

There have also been proposals to use a combination of two adjuvants substances in an adjuvant composition. For example, Australian patent no. 602348 describes an immunoadjuvant comprising an immunoadjuvant oil substantially free of mycobacteria and a polycationic polyelectrolyte immunoadjuvant such as DEAE dextran in the form of an emulsion having the polycationic polyelectrolyte dissolved in the aqueous phase. The two-component immunoadjuvant is said to overcome the rapid decline in the immune response associated with polycationic polyelectrolyte adjuvants on the one hand and, on the other, the weak initial response associated with immunoadjuvant oils. Accordingly, the two-component adjuvant is said to fill the gap in the prior art between those adjuvants inducing high peak/short life antibody responses and those inducing low peak/long life responses.

International application no. 88/07547 is primarily concerned with a novel peptide nevertheless, it also discloses the use of a novel adjuvant comprising DEAE dextran and a saponin or aluminium hydroxide and notes an improved antibody titre when the two-component immunoadjuvants are used. In particular, solutions of DEAE dextran and saponin in phosphate buffered saline are used but there is no suggestion of the incorporation of an immunoadjavent oil into such compositions.

Australian patent no. 640414 discloses a solid vaccine composition comprising an antigenic substance capable of inducing the generation of antibodies on parenteral administration to an animal, a saponin and a polycationic adjuvant. The essence of the invention is that the vaccine is formulated as solid to be implanted in the animal to thereby induce a long-lasting immune response. There is no suggestion of the presence of an immunoadjuvants oil in the composition and, indeed, the specification teaches away from the use of an oil as it is critical to the invention that this formulation be solid.

In the present invention it has been found, surprisingly, that combinations of certain adjuvants enhance the effectiveness of an antigenic substance in stimulating an immune response to a much greater extent than the sum of the profiles that would be obtained by the use of the components separately or through the use of a two-component immunoadjuvant.

DISCLOSURE OF THE INVENTION

According to a first aspect of the present invention there is provided an adjuvant composition for stimulating an effective immune response in an animal to an antigenic substance when co-administered to said animal with said antigenic substance, comprising:
  (a) a saponin with immune stimulating activity;
  (b) a polycationic polyelectrolyte with immune stimulating activity; and
  (c) an immunoadjuvant oil.

According to a second aspect of the present invention there is provided a vaccine for administration to an animal, comprising:
  (1) an antigenic substance; and
  (2) an adjuvant composition comprising:
    (a) a saponin with immune stimulating activity;
    (b) a polycationic polyelectrolyte with immune stimulating activity;
    (c) an immunoadjuvant oil.

According to a third aspect of the present invention there is provided a method of stimulating an effective immune response in an animal to an antigenic substance, comprising the steps of:
  (1) providing said antigenic substance;
  (2) providing an adjuvant composition for stimulating an effective immune response to said antigenic substance, comprising:

(a) a saponin with immune stimulating activity;
(b) a polycationic polyelectrolyte with immune stimulating activity; and
(c) an immunoadjuvant oil; and
(3) challenging said animal with said antigenic substance and said adjuvant composition.

According to a fourth aspect of the present invention there is provided the use of an adjuvant composition comprising:
(a) a saponin with immune stimulating activity;
(b) a polycationic polyelectrolyte with immune stimulating activity; and
(c) an immunoadjuvant oil to stimulate an effective immune response in an animal challenged with an antigenic substance.

According to a fifth aspect of the present invention there is provided the use of an adjuvant composition comprising:
(a) a saponin with immune stimulating activity;
(b) a polycationic polyelectrolyte with immune stimulating activity; and
(c) an immunoadjuvant oil in the preparation of a medicament for administration to an animal, wherein said medicament further comprises an antigenic substance.

The saponins are common secondary constituents of plants and typically are glycosides composed of several (hydrophilic) sugars in association with a (hydrophobic) molecule, which can be either a steroid or triterpenoid structure. In particular, an extract from the South American tree *Quillaja saponarioa* shows good adjuvant activity and is now denoted "Quil A". While the precise chemical composition of Quil A is not known, the sugar moieties detected in the mixture include rhamnose, fucose, arabinose, xylose, galactose, glucose, apiose and glucuronic acid and the hydrophobic moiety has a triterpenoid structure. The nature of Quil A is discussed as length in Australian patent application no. 10777/95, the disclosure of which is incorporated herein by reference.

Preferably, the saponin is a triterpenoid compound or a mixture of triterpenoid compounds. More preferably, the saponin is Quil A or the extract disclosed in Australian application no. 10777/95, or compounds obtainable from these extracts. Still more preferably, the saponin is Quil A.

As used throughout the description and claims the term "polycationic polyelectrolyte" refers to polymer or oligomers, natural or synthetic, that, by virtue of their chemical structure, acquire a plurality of discrete positive charges in aqueous solution under appropriate pH conditions. Suitable polycationic polyelectrolytes are DEAB dextran, polyethyleneimine, ethoxylated polyethyleneimine, epichlorhydrin-modified polyethyleneimine, diethylaminoethyl ester and amide derivatives of acrylate polymers, copolymers and the like. The most preferable polycationic polyelectrolyte is DEAE dextran, which is a polycationic derivative of dextran (average molecular weight 10000 to 1000000, preferably 200000 to 750000, most preferably 500000) containing diethylamino ethyl groups linked to glucose in a 1:3 ratio. Typically the polycationic polyelectrolyte is in aqueous solution, for example, phosphate buffered saline.

While the invention embraces a wide range of immunoadjuvant oils, mineral oils are preferred. More preferred are those mineral oils already known in the art for use as adjuvants and including substances such as Drakeol, Markol, squalene, squalane and the like but the preferred mineral oil is Montanide oil. Mineral oil immunoadjuvants are frequently referred to as Freund's incomplete adjuvant and this adjuvant typically comprises 85% mineral oil and 15% mannide monooleate as an emulsifier.

Typically the adjuvant composition of the present invention takes the form of an emulsion with the polycationic polyelectrolyte dissolved in the aqueous phase and the mineral oil forming the non-aqueous phase. It is well known that immunoadjuvant emulsions of individual oils used separately can be formulated with oil to water phase ratios extending over a broad range and embracing the ratios 80:20 to 20:80 (v/v) for example, more preferably 60:40 to 40:60 (v/v). Such a broad range of ratios of oil phase to aqueous phase also applies in the present invention except that the aqueous phase will always comprise a polycationic polyelectrolyte solution and the composition will also include a saponin. While not wishing to be bound by theory, the saponin is amphiphilic and which may partition itself between the phases with the hydrophilic sugar residues in the aqueous phase and the hydrophobic triterpenoid structure in the non-aqueous phase. Accordingly, the saponin may serve to stabilise the emulsion.

Preferably, vaccines including adjuvant compositions in accordance with the present invention contain the saponin component at a concentration greater than 50 μg/ml and the polycationic polyelectrolyte at a concentration of greater than 1 mg/ml. More preferably, they contain saponins in a concentration of greater than 100 μg/ml and the polycationic polyelectrolyte component in a concentration of greater than 1.5 mg/ml. The upper limits of concentration of the saponin component and the polycationic polyelectrolyte are essentially determined by economic considerations since these components are expensive, but the saponin may be present in concentrations up to 10 mg/ml, typically up to 1 mg/ml, and the polycationic polyelectrolyte may be present in concentrations up to 200 mg/ml, typically 150 mg/ml.

The emulsifiers used to form the novel compositions of the invention are those known in the art such as mannide monooleate, Arlacela A, Arlacela 80 and Tween 80. It will be recognised by those skilled in the art that the adjuvant composition can be used in virtually any vaccine including any antigenic substance, although it will be recognised that many factors other than the nature of the adjuvant composition will influence the nature of and level of the antibody response to the vaccine.

The adjuvant composition is particularly useful when used in conjunction with a whole cell killed vaccine or killed viral vaccine or a vaccine comprising a proteinaceous substance, which may or may not be glyocosylated or otherwise chemically modified, alone or as a carrier for a low molecular weight compound. In general, the antigenic substance will give rise to an immune response against a disease-causing agent but may also give rise to antibodies against an agent (such as a hormone) which does not normally give rise to a disease. The disease causing agent may be a structural component or toxin of a virus, bacteria or other microbe. Examples of virally-caused diseases which may be controlled by vaccines including the adjuvant composition of the present invention include infectious bursal disease virus, Newcastle disease, infectious bronchitis virus, pseudorabies, parvovirus, classical swine fever, equine influenza, bovine viral diarrhoea virus and canine corona virus. Examples of bacterially-caused diseases include atrophic rhinitis, loptospirosis, clostridial infections, bordetella brochisepticum infections in cats, coryza in poultry, fowl chloera, Mycoplasma gallisepticum infections in poultry, pleuropmeumonia and rabies. The adjuvant composition may also be used in conjunction with sub-unit vaccines produced using recombinant DNA technology such as in a sub-unit vaccine against cattle ticks.

The antigenic substance may also comprise a target low molecular weight compound conjugated to a carrier selected so as not to be recognised by the organism as "self" and thereby to generate an immune response against the low molecular weight compound. Suitable carriers include fetuin, ovalbumin, bovine serum albumin, foetal calf serum and human serum albumin. Alternatively, the carrier may be keyhole limpet haemocyanin or beta-galactosidase, among others. The low molecular weight compound may be conjugated to the carrier by any convenient means. Suitable conjugators include glutaraldehyde, toluene diisocyanate, carbodiimide, or any other suitable conjugator.

The small molecules which may be conjugated to a character include toxins such as phomopsin or other substances such as mammaliam hormones or steroids against which it may be desirable to raise an immune response.

Other antigens which may be employed include red blood cells and virus like particles, particularly VLP/NS2.

Preferably, the antigenic substance is a fetuin-phomopsin conjugate, phomopsin A conjugated to ovalbumin, phomopsin A-fetal calf serum conjugate, a virus-like particle, particularly VLP/NS2 (a VLP comprising a blue tongue virus antigen encoded by a recombinant baculovirus vector), sheep red blood cells, or ovalbumin.

In the method of the invention the antigenic substance and adjuvant composition are conveniently mixed prior to administration. Typically, the antigenic substance is in aqueous solution, such as phosphate-buffered saline. The polycationic polyelectrolyte may also be in aqueous solution, such as in solution in phosphate-buffered saline, and together these components form the aqueous phase of the emulsion. However, it will be appreciated that the antigenic substance and adjuvant may be administered sequentially, and even that the various components of the adjuvant composition may be administered sequentially rather than simultaneously provided that they undergo a physiological interaction in vivo.

Throughout the specification, except where the context requires otherwise due to express language or necessary implication, the word "comprising" is used in the sense of "including", ie. the features specified may be associated with further features in various embodiments of the invention and are not to be construed, necessarily, as the only features of the invention.

BRIEF DESCRIPTION OF THE DRAWINGS

The present invention will now be further described, by way of example only, with reference to the accompanying drawings, in which:

FIG. 1 shows the antibody response to sheep red blood cells in chickens in a Haemagglutination assay;

FIG. 2 shows the antibody response to sheep red blood cells in chickens in an ELISA assay on 0.1 ml of 0.1% sheep red blood cells/well coated plate;

FIG. 3 shows the antibody response to phomopsins in cattle in an ELISA assay on 50 ng phomopsins/1.0 ml/well coated plate;

FIG. 4 shows the antibody response to ovalbumin in cattle in an ELISA assay on 50 ng ovalbumin/1.0 ml/well coated plate;

FIG. 5 shows the antibody response to phomopsins in wethers in an ELISA assay on 50 ng phomopsins/1.0 ml/well coated plate;

FIG. 6 shows the antibody response to foetal calf serum in wethers in an ELISA assay on 50 ng foetal calf serum/1.0 ml/well coated plate; and FIG. 7 shows the antibody response to ovalbumin in Long-Evans hooded rats using an ELISA assay on 50 ng ovalbumins/0.1 ml/well coated plate.

MODES OF CARRYING OUT THE INVENTION

EXAMPLE 1

In this example a fetuin-phomopsin conjugate was employed as the antigen in a comparison of three adjuvant formulations including one formulation conforming to the invention described in this specification. Sheep (12 per group) were the animal species used. The dose volume (1 ml) and antigen concentration were kept constant and the oil component was 85% (v/v) mineral oil and 15% (v/v) mannide monooleate (incomplete Freund's adjuvant, ICF) in all formulations.

In one formulation the adjuvant comprised a 10 mg/dose of DEAE dextran as the cationic polymer in incomplete Freund's oil (10 mg DEAE/ICF). In another the adjuvant was 0.5 mg Quil A as a triterpenoid component in incomplete Freund's oil (0.5 mg Quil A/ICF) and in the third, representative of this invention, 5 mg of DEAE and 0.5 mg of Quil A were mixed together in incomplete Freund's oil (0.5 mg Quil A/5 mg DEAE/ICF). A primary and one booster injection were administered 16 weeks apart. Anti-phomopsin antibody titres (measured by ELISA) were not detectable prior to vaccination. Table 1 shows anti-phomopsin antibody titres 2 and 8 weeks after the booster injection.

TABLE 1

| Adjuvant formulation | Dose volume | Sheep Nos. | Titre - Booster plus 2 weeks | Titre - Booster plus 8 weeks |
|---|---|---|---|---|
| 10 mg DEAE/ICF | 1 ml | 12 | 55,000 | 8,000 |
| 0.5 mg Quil A/ ICF | 1 ml | 12 | 23,000 | 2,000 |
| 0.5 mg Quil A/ 5 mg DEAE/ICF | 1 ml | 12 | 99,000 | 37,000 |

The results show that the trivalent adjuvant prepared according to this invention gave a significantly higher antibody titre two weeks after the booster injection than either of the divalent formulations lacking one component of the trivalent formulation. The titre obtained with the trivalent adjuvant was also greater than the sum of the titres produced by the two divalent formulations demonstrating an unexpected synergism between the components. Eight weeks after the booster injection the trivalent vaccine was outperforming the divalent formulations by an increased margin demonstrating the longer duration of effect and the synergistic response achieved.

EXAMPLE 2

In another comparison of two, two-component mixtures and a three component mixture representative of this invention, three groups of 12 sheep were injected with a fetuin-phomopsin conjugate antigen formulated in an adjuvant mixture of DEAE dextran in incomplete Freund's adjuvant (ICF) or Quil A in ICF or a mixture of DEAE dextran and Quil A in ICF. The antibody titres achieved are shown in Table 2.

TABLE 2

| Adjuvant formulation | Dose volume | Sheep Nos. | Titre - Booster plus 2 weeks | Titre - Booster plus 8 weeks |
|---|---|---|---|---|
| 10 mg DEAE/ICF | 1 ml | 12 | 8,000 | 2,000 |
| 0.5 mg Quil A/ ICF | 1 ml | 12 | 9,000 | 1,000 |
| 0.5 mg Quil A/5 mg DEAE/ICF | 1 ml | 12 | 44,000 | 14,000 |

Once again the adjuvant formulated according to this invention demonstrates an enhanced, synergistic, long-lasting effect when compared to two component formulations in which one of the three components specified in this invention is missing.

EXAMPLE 3

In this example a comparison was made between two trivalent adjuvant formulations incorporating a triterpinoid (Quil A), a cationic polymer (DEAE dextran) and two different commercially available oils (ICF or Montanide 888). Both formulations incorporated a commercial preservative, Thimerosal, and the antigen was a phomopsin fetuin conjugate. The results are shown in Table 3

TABLE 3

| Adjuvant formulation | Dose volume | Sheep Nos. | Anti-phomopsin titre - Booster plus 2 weeks | Anti-phomopsin titre - Booster plus 8 weeks |
|---|---|---|---|---|
| 0.5 mg Quil A/5 mg DEAE/ICF | 1 ml | 11 | 20,000 | 16,000 |
| 0.5 mg Quil A/5 mg DEAE/Montanide 888 | 1 ml | 11 | 40,000 | 25,000 |

The results demonstrate the high titres obtained with this invention and the longevity of the effect with both formulations. A better response is seen with the Montanide oil under the conditions used demonstrating that careful selection of the oil component of the invention from a number of available products can give advantage for particular applications.

EXAMPLE 4

Animal Species: Rabbit
The Antigen: Virus-like Particles (VLPs).
Adjuvant Formulations:
This invention. 2.5 mg Quil A and 50 mg DEAE-dextran in 3 ml of PBSA was filtered through a 0.2 μm filter. Six hundred microlitres of this solution was added to 200 microlitres of antigen (1 mg VLP/NS2, a VLP comprising a blue tongue virus antigen encoded by a recombinant baculovirus vector, pelleted and resuspended in 200 microlitres PBSA). 1.2 ml of Montanide ISA 50V was then added to this combined solution. The mixture was sonicated and emulsified to form a viscous liquid.

Freund's complete. 1 ml Freund's Complete adjuvant was added to 1 ml VLP/NS2 (1 mg) in PBSA. This solution was sonicated and emulsified. An extremely viscous, almost solid emulsion was formed.

Freund's incomplete/DEAE dextran. 1 mg VLP/NS2 was resuspended in 15 ml of 15% DEAE-dextran and added to 1 ml of Freund's incomplete adjuvant. This solution was sonicated and emulsified.

PBSA. VLP/NS2 was dissolved in PBSA at a concentration of 1 mg per ml.

Vaccination Protocols

This invention. Five 0.1 ml intradermal injections per rabbit were given for the primary vaccination and 0.3 ml in each hind leg were given for the booster.

Freund's complete. Four intradermal injections of 0.1 ml were given as the primary vaccination and 0.4 ml intramuscular injection per hind leg was given as a booster.

Freund's incomtplete/DEAE dextran. Five intradermal injections were given per rabbit were given as the primary vaccination and 0.3 ml per hind leg were given as a booster.

PBSA. A 0.5 ml intramuscular injection was given to each hind legs for both the primary and booster injections.

The rabbits were bled on day 1 and injections were given on day 5, day 54, and day 78.

This example demonstrates that the adjuvant composition of the present invention performs very well when compared to Freund's adjuvant. In the data shown in Table 4 it will be apparent that the immune response using the adjuvant of the present invention begins earlier than the immune response when Freund's adjuvant is used and is stronger and more long lasting. In addition, the adjuvant does not induce the formation of lesions at the injection site as Freund's adjuvant can.

Results.

The antibody titres achieved for each protocol are given in Table 4.

TABLE 4

| Rabbit | Day 1 | Day 20 | Day 44 | Day 61 | Day 72 | Day 89 | Day 96 | Day 109 | Day 123 |
|---|---|---|---|---|---|---|---|---|---|
| This invention | 0 | 1000 | 5000 | >50000 | >50000 | >50000 | >50000 | >50000 | 25000 |
| This invention | 0 | 25000 | 25000 | >50000 | >50000 | >50000 | 25000 | 5000 | 1000 |
| Freund's | 0 | 0 | 5000 | 5000 | 25000 | >50000 | 25000 | 25000 | 1000 |
| Freund's | 0 | 0 | 1000 | 1000 | 5000 | 25000 | >50000 | 5000 | 5000 |
| ICF | 0 | 0 | 5000 | 25000 | 50000 | 25000 | 5000 | 5000 | 1000 |
| ICF | 0 | 1000 | 5000 | 5000 | 5000 | >50000 | 25000 | 25000 | 5000 |
| PBS | 0 | 0 | 1000 | 5000 | 1000 | 1000 | 5000 | 1000 | 1000 |
| PBS | 0 | 0 | 1000 | 50000 | 5000 | 5000 | 5000 | 1000 | 0 |

The results demonstrate the effectiveness of an adjuvant encompassed by this invention compared to Freund's complete adjuvant, ICF and the antigen injected in PBSA as a control.

EXAMPLE 5

In this example a comparison was made between the immune response and injection site reaction of chickens to sheep red blood cells. The red blood cells were administered either in Freund's complete adjuvant with a booster injection, in incomplete Freund's adjuvant or in an adjuvant system typifying this invention for both primary and booster injections.

Sterile sheep blood (100 ml) was collected and 1 volume of blood was added immediately into 1.2 volume of Alsever's solution (Methods in Immunology and Immunochemistry, vol 4, 41, Eds: Williams, C. A. and Chase, M. W., 1977).

Hybrid white leghorn chickens eggs (Ex SPF Unit) were set on 2/10/97 and chickens were hatched 21 days later.

Five week old chickens were weighed and divided into two groups of 12. 0.5 to 1 ml blood was collected from the wing vein of each chicken prior to vaccination. For the primary injections formulated using an adjuvant typifying that described in this invention, 0.1 ml of sheep red blood cells were added to 0.1 ml of phosphate buffered saline containing 62.5 μg Quil A, 1.25 mg DEAE-dextran and emulsified with 0.3 ml of Montanide 888 oil (60%). In the comparison group, 0.1 ml of sheep red blood cells were added to 0.15 ml of phosphate buffered saline and emulsified with 0.25 ml of Complete Freund's adjuvant (50%). In both groups, the total volume injected was 0.5 ml per dose. It was administered in equal volumes to the thigh muscles of both legs.

After two weeks the chickens were weighed, tissue reactions at the injection sites were inspected and 0.5 to 1 ml blood was collected from wing vein.

After a further 13 days the chickens were weighed once again, tissue reactions at the injection sites were inspected and 0.5 to 1 ml blood was collected from wing vein. After the inspection a booster injection of 0.1 ml of sheep red blood cells was given intra muscularly in both adjuvants as for the primary injection but incomplete Freund's adjuvant was employed in the comparison group.

Two weeks later the chickens were weighed, tissue reactions at the injection sites were inspected and 0.5 to 1 ml blood was collected from wing vein.

Eight weeks after the booster injection the chickens were weighed, tissue reactions at the injection sites were inspected and 0.5 to 1 ml blood was collected from wing vein.

Haemagglutination Assay

Chickens sera were incubated at 56° C. for 30 minutes to inactivate complement. Fifty μl of phosphate buffered saline was added to all wells of row 1 to 12 of 96 wells, U-shaped bottom, microtest plates (Sarstedt, Australia). Fifty μl of heat inactivated sera, before and after the immunisation, were added to wells of the first row. Two fold serial dilutions were performed across the plates. Fifty μl of 2% sheep red blood cells suspension was added to all wells. The plates were shaken for 1 minute, covered and incubated at 4° C. for 2 hours. Titres were expressed as the reciprocal of the highest dilution resulting in complete agglutination.

ELISA on Sheep Red Blood Cells Coated Microtitre Plates

Sheep red blood cells were diluted as 0.1% in carbonate coating buffer pH 9.6 and 100 μl of the solution was added to all wells of row 2 to 12 of 96 wells, flat bottom, microtitre plates (Nunc-Immuno plate, F 96 polysorp, Cat. 475094). After overnight incubation at 4° C., the plates were washed four times with 0.05% tween 20 in saline. After the washing, 100 μl of 0.1% gelatine in phosphate buffered saline was added to all wells of row 2 to 12 of microtitre plates. Which was followed by the addition of the reference serum and sera for testing, diluted 1/100 in 0.1% gelatine in phosphate buffered saline, to the wells of row 2. Two fold serial dilutions were performed across the plates. After 2 hours incubation at room temperature, the plates were washed four times and 100 μl of 1/20,000 anti-chicken IgG, developed in rabbit, conjugated to peroxidase (Sigma Cat. A 9046) was added and incubated for a further 1 hour. After washing the plate four times 3, 3', 51 5'-tetramethylbenzidine (Sigma Cat. T2885) substrate was added and incubated for a further 15 minutes before the stopping solution was added. Titres were expressed as the reciprocal of the dilution resulting in 0.5 optical density of the wells.

Figure 2:
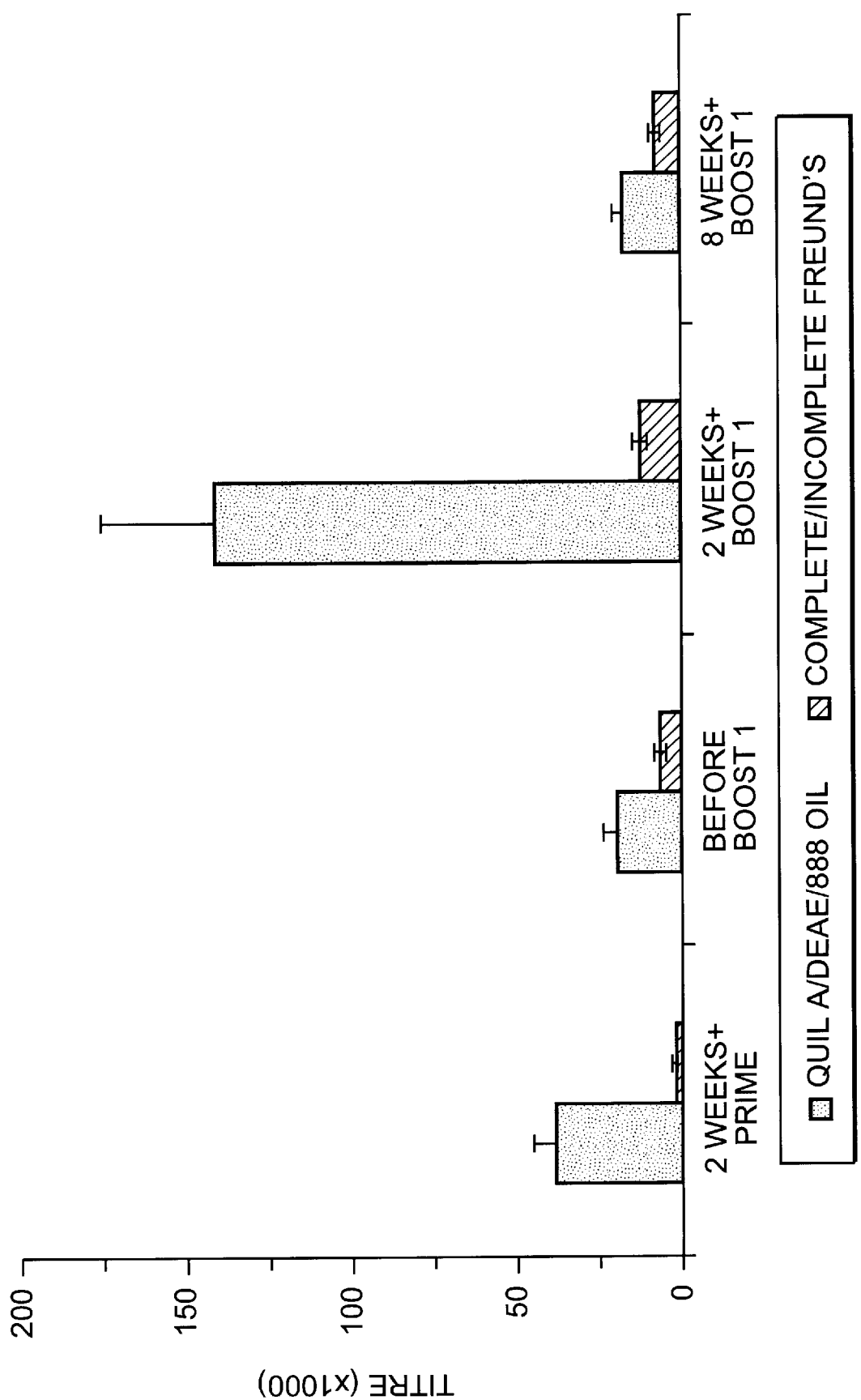

The results of the experiment are shown in FIG. 1 and 2 and Tables 5 to 7.

TABLE 5

Adjuvant experiment in chickens (hybrid white leghorn)

| Adjuvant | Iso-lator | Pink No. | Sex | Weight (gm) | | | | | Tissue reaction | Tissue reaction | Remark |
|---|---|---|---|---|---|---|---|---|---|---|---|
| | | | | Before prime | 2 weeks after prime | Before boost 1 | 2 weeks after boost 1 | 8 weeks after boost 1 | 2 weeks after prime | 2 weeks after boost 1 | 8 weeks after boost 1 |
| (Quil A | 4 | 41 | Female | 310 | 500 | 680 | 909 | 1372 | | | |
| DEAE/ | 4 | 42 | Female | 315 | 529 | 722 | 940 | 1399 | | | |
| 888 oil) | 4 | 43 | Female | 285 | 464 | 617 | 845 | 1298 | | | |
| | 4 | 44 | Male | 336 | 584 | 794 | 1156 | 1875 | | | |
| | 4 | 45 | Male | 433 | 715 | 955 | 1322 | 2137 | | | |
| | 4 | 46 | Male | 345 | 586 | 738 | 1084 | 1663 | | | |
| | 3 | 47 | Female | 287 | 475 | 645 | 841 | 977 | | | Head pecked by others |
| | 3 | 48 | Female | 361 | 590 | 767 | 941 | 1290 | | | |
| | 3 | 49 | Female | 309 | 408 | 646 | 831 | 1162 | | | |
| | 3 | 50 | Male | 398 | 651 | 895 | 1159 | 1585 | | | |
| | 3 | 51 | Male | 390 | 675 | 946 | 1307 | 1832 | | | |
| | 3 | 52 | Male | 439 | 726 | 1047 | 1303 | 1980 | | | |
| Mean | | | | 351 | 575 | 786 | 1053 | 1548 | | | |
| SD | | | | 54 | 103 | 143 | 192 | 356 | | | |
| Counts | | | | 12 | 12 | 12 | 12 | 12 | | | |

TABLE 5-continued

Adjuvant experiment in chickens (hybrid white leghorn)

| SE | | | 18 | 30 | 41 | 55 | 103 | | | |
|---|---|---|---|---|---|---|---|---|---|---|
| | | | | Weight (gm) | | | | Tissue reaction | Tissue reaction | Tissue reaction |
| Adjuvant | Iso-lator | Yellow No. | Sex | Before prime | 2 weeks after prime | Before boost 1 | 2 weeks after boost 1 | 8 weeks after boost 1 | 2 weeks after prime | 2 weeks after boost 1 | 8 weeks after boost 1 |
| CF/ICF | 4 | 1 | Female | 313 | 527 | 700 | 953 | 1435 | | | |
| | 4 | 2 | Female | 310 | 482 | 610 | 843 | 1184 | | | |
| | 4 | 3 | Female | 308 | 511 | 680 | 940 | 1318 | | | |
| | 4 | 4 | Male | 354 | 636 | 834 | 1185 | 1904 | Lump on left leg | Lump on left leg | |
| | 4 | 5 | Male | 323 | 573 | 755 | 1092 | 1884 | | | |
| | 4 | 6 | Male | 368 | 664 | 830 | 1160 | 2006 | | | |
| | 3 | 7 | Female | 317 | 518 | 680 | 902 | 970 | | | Head pecked by others |
| | 3 | 8 | Female | 315 | 518 | 736 | 956 | 1397 | | | |
| | 3 | 9 | Female | 348 | 557 | 752 | 986 | 1416 | | | |
| | 3 | 10 | Male | 415 | 706 | 1002 | 1325 | 1965 | | | |
| | 3 | 11 | Male | 420 | 724 | 1033 | 1356 | 1957 | | | |
| | 3 | 12 | Male | 279 | 463 | 714 | 931 | 1458 | | | Head pecked by others |
| Mean | | | | 339 | 573 | 777 | 1052 | 1575 | | | |
| SD | | | | 44 | 88 | 128 | 169 | 352 | | | |
| Counts | | | | 12 | 12 | 12 | 12 | 12 | | | |
| SE | | | | 13 | 25 | 37 | 49 | 102 | | | |

TABLE 6

Adjuvant experiment in chickens (hybrid white leghorn)

| | | | | Titre using haemagglutination assay (reciprocal dilution) | | | |
|---|---|---|---|---|---|---|---|
| Adjuvant | Isolator | Pink no. | Sex | 2 weeks after prime | Before boost 1 | 2 weeks after boost 1 | 8 weeks after boost 1 |
| (Quil A/ | 4 | 41 | Female | 32 | 4 | 16 | 8 |
| DEAE/ | 4 | 42 | Female | 16 | 8 | 64 | 8 |
| 888 oil) | 4 | 43 | Female | 8 | 8 | 64 | 16 |
| | 4 | 44 | Male | 32 | 8 | 32 | 4 |
| | 4 | 45 | Male | 16 | 4 | 16 | 4 |
| | 4 | 46 | Male | 16 | 8 | 16 | 4 |
| | 3 | 47 | Female | 64 | 16 | 64 | 2 |
| | 3 | 48 | Female | 64 | 32 | 128 | 16 |
| | 3 | 49 | Female | 8 | 8 | 64 | 8 |
| | 3 | 50 | Male | 64 | 8 | 32 | 4 |
| | 3 | 51 | Male | 16 | 8 | 32 | 4 |
| | 3 | 52 | Male | 64 | 16 | 128 | 16 |
| Mean | | | | 33 | 11 | 55 | 8 |
| SD | | | | 24 | 8 | 39 | 5 |
| Counts | | | | 12 | 12 | 12 | 12 |
| SE | | | | 7 | 2 | 11 | 2 |

| | | | | Titre using haemagglutination assay (reciprocal dilution) | | | |
|---|---|---|---|---|---|---|---|
| Adjuvant | Isolator | Yellow no. | Sex | 2 weeks after prime | Before boost 1 | 2 weeks after boost 1 | 8 weeks after boost 1 |
| CF/ICF | 4 | 1 | Female | 4 | 4 | 8 | 8 |
| | 4 | 2 | Female | 8 | 2 | 4 | 4 |
| | 4 | 3 | Female | 4 | 2 | 8 | 4 |
| | 4 | 4 | Male | 4 | 8 | 32 | 32 |
| | 4 | 5 | Male | 16 | 16 | 16 | 4 |
| | 4 | 6 | Male | 4 | 4 | 8 | 4 |
| | 3 | 7 | Female | 16 | 8 | 32 | 4 |
| | 3 | 8 | Female | 16 | 4 | 16 | 32 |
| | 3 | 9 | Female | 16 | 16 | 64 | 64 |
| | 3 | 10 | Male | 4 | 32 | 32 | 8 |
| | 3 | 11 | Male | 8 | 8 | 8 | 4 |
| | 3 | 12 | Male | 2 | 2 | 16 | 8 |
| Mean | | | | 9 | 9 | 20 | 15 |
| SD | | | | 6 | 9 | 17 | 19 |

TABLE 6-continued

Adjuvant experiment in chickens (hybrid white leghorn)

| | | | | |
|---|---|---|---|---|
| Counts | 12 | 12 | 12 | 12 |
| SE | 2 | 3 | 5 | 5 |

TABLE 7

Adjuvant experiment in chickens (hybrid white leghorn)

| | | | | Titre using ELISA (× 1000) | | | |
|---|---|---|---|---|---|---|---|
| Adjuvant | Isolator | Pink no | Sex | 2 weeks after prime | Before boost 1 | 2 weeks after boost 1 | 8 weeks after boost 1 |
| (Quil A/ | 4 | 41 | Female | 35 | 12 | 85 | 11 |
| DEAE/ | 4 | 42 | Female | 22 | 9 | 115 | 14 |
| 888 oil) | 4 | 43 | Female | 36 | 20 | 43 | 21 |
| | 4 | 44 | Male | 36 | 18 | 189 | 12 |
| | 4 | 45 | Male | 19 | 13 | 42 | 15 |
| | 4 | 46 | Male | 106 | 35 | 431 | 17 |
| | 3 | 47 | Female | 54 | 24 | 250 | 21 |
| | 3 | 48 | Female | 36 | 15 | 82 | 33 |
| | 3 | 49 | Female | 5 | 4 | 34 | 10 |
| | 3 | 50 | Male | 34 | 42 | 191 | 27 |
| | 3 | 51 | Male | 20 | 14 | 42 | 10 |
| | 3 | 52 | Male | 60 | 32 | 191 | 20 |
| Mean | | | | 38 | 20 | 141 | 18 |
| SD | | | | 26 | 11 | 117 | 7 |
| Counts | | | | 12 | 12 | 12 | 12 |
| SE | | | | 8 | 3 | 34 | 2 |

| | | | | Titre using ELISA (× 1000) | | | |
|---|---|---|---|---|---|---|---|
| Adjuvant | Isolator | Yellow no | Sex | 2 weeks after prime | Before boost 1 | 2 weeks after boost 1 | 8 weeks after boost 1 |
| CF/ICF | 4 | 1 | Female | 1 | 3 | 9 | 4 |
| | 4 | 2 | Female | 2 | 2 | 5 | 6 |
| | 4 | 3 | Female | 2 | 2 | 7 | 8 |
| | 4 | 4 | Male | 1 | 5 | 17 | 10 |
| | 4 | 5 | Male | 6 | 19 | 22 | 5 |
| | 4 | 6 | Male | 3 | 4 | 12 | 8 |
| | 3 | 7 | Female | 2 | 3 | 12 | 6 |
| | 3 | 8 | Female | 2 | 4 | 5 | 6 |
| | 3 | 9 | Female | 2 | 9 | 15 | 14 |
| | 3 | 10 | Male | 1 | 15 | 29 | 6 |
| | 3 | 11 | Male | 2 | 9 | 13 | 8 |
| | 3 | 12 | Male | 0 | 1 | 4 | 3 |
| Mean | | | | 2 | 6 | 12 | 7 |
| SD | | | | 1 | 6 | 7 | 3 |
| Counts | | | | 12 | 12 | 12 | 12 |
| SE | | | | 0 | 2 | 2 | 1 |

EXAMPLE 6

In this example a comparison was made between cattle injected with phomopsin A conjugated to ovalbumin in Freund's complete adjuvant with a booster injection of the conjugate antigen in incomplete Freund's adjuvant or with the same antigen delivered in an adjuvant prepared according to this invention.

Twenty four, five months old cattle were weighed and two 10 ml samples of blood were collected from each animal. All the cattle also received 4 ml of five in one vaccine, injected subcutaneously to the left side of the back of the neck.

Two weeks later the cattle were weighed and divided into two randomised groups. The animals were then given a primary injection. The animals in one group received an injection of 100 µg phomopsin A conjugated to 336 µg ovalbumin, 1 mg Quil A and 10 mg DEAE-dextran dissolved in 0.8 ml of sterile water and emulsified with 1.2 ml of Montanide 888 oil (60%). The animals in the other group were injected with 100 µg phomopsin A conjugated to 336 µg ovalbumin dissolved in 1 ml of sterile water, and emulsified with 1 ml of Complete FreundIs adjuvant (50%). In both groups, immunogens were injected subcutaneously as a total volume of 2 ml to the right side of the back of the neck, below the ear.

Thirteen days later tissue reactions at the injection sites were inspected and 10 ml blood was collected from jugular vein.

After four weeks cattle were weighed, tissue reactions at the injection sites were inspected and 10 ml blood was collected from jugular vein. A booster injection of 100 µg phomopsin A conjugated to 440 µg foetal calf serum was given subcutaneously as in primary injection. In the case of the comparison group this was formulated in Incomplete Freund's Adjuvant. A second dose of five in one vaccine was also injected subcutaneously to the left side of the back of the neck.

Two weeks later tissue reactions at the injection sites were inspected and 10 ml blood was collected from jugular vein.

Eight weeks after the booster injection cattle were weighed and tissue reactions at the injection sites were inspected and 10 ml blood was collected from jugular vein.
ELISA on 50 ng Phomopsins/well Coated Microtitre Plates Phomopsins were diluted as 50 ng/100 µl in carbonate coating buffer pH 9.6 and 100 µl of the solution was added to all wells of row 2 to 12 of 96 wells, flat bottom, microtitre plates (Sarstedt, Australia). After overnight incubation at 40° C., the plates were washed four times with 0.05% tween 20 in saline. After the washing, 100 µl of 0.1% gelatine in phosphate buffered saline was added to all wells of microtiter plates. Reference serum and sera for testing, diluted 1/100 in 0.1% gelatine in phosphate buffered saline, were then added to the wells of row 2. Two fold serial dilutions were performed across the plates. After 2 hours incubation at room temperature, the plates were washed four times and 100 µl of 1/15,000 anti-bovine IgG, developed in rabbit, conjugated to peroxidase (Sigma Cat.B 1520) was added and incubated for a further 2 hour. After washing the plate four times 3, 3', 5, 51'-tetramethylbenzidine (Sigma Cat. T2885) substrate was added and incubated for a further 20 minutes before the stopping solution was added. Titres were expressed as the reciprocal of the dilution resulting in 0.5 optical density of the wells.

ELISA on 50 ng ovalbumin/well coated microtitre plates
ELISA was also performed on 50 ng ovalbumin/well coated plates as above in phomopsins 50 ng/well coated plates except 96 wells, flat bottom, Nunc-Immuno maxisorp microtitre plates (Cat. 439454) were used for the assay.

Figure 3:
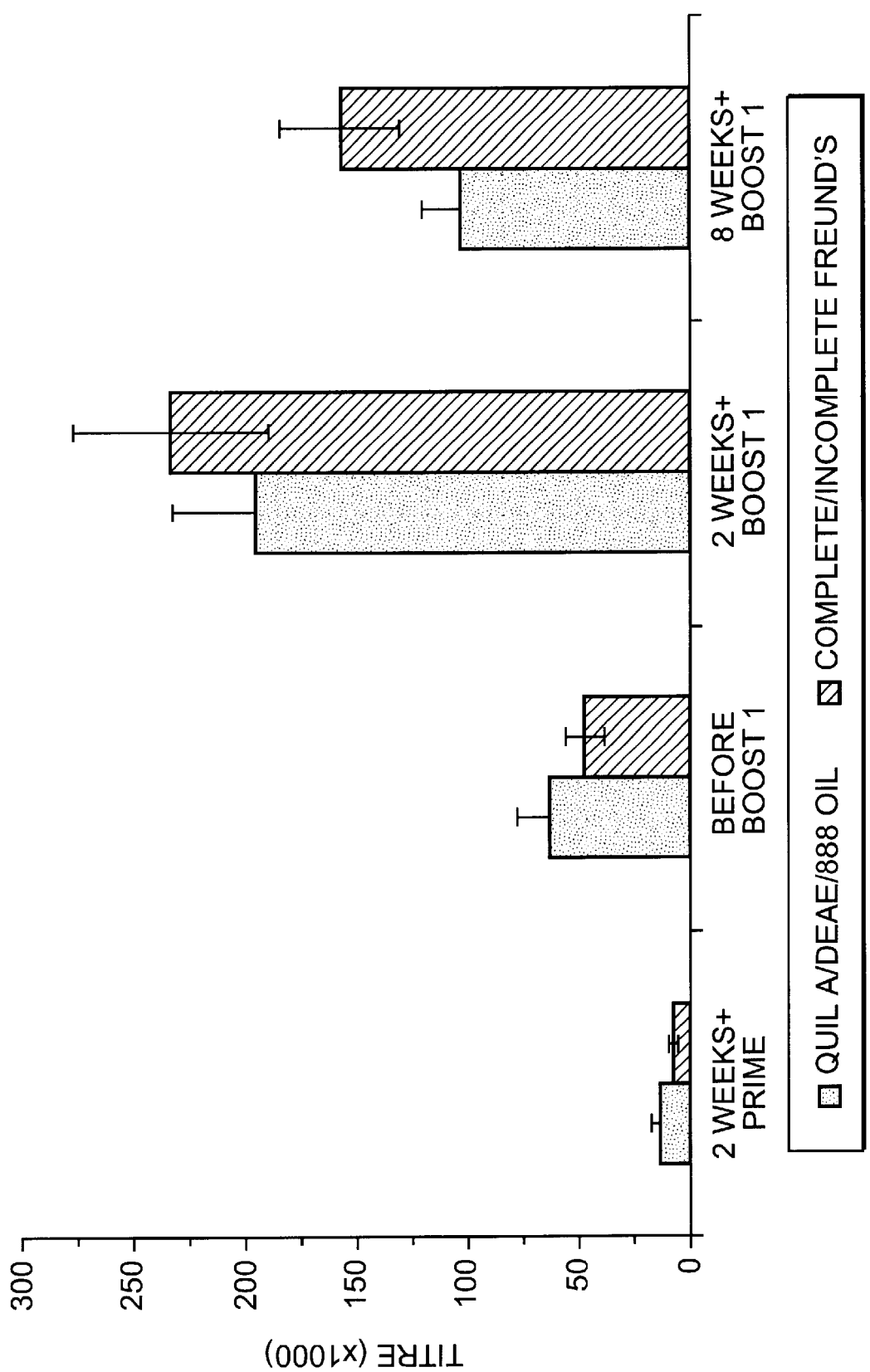
Figure 4:
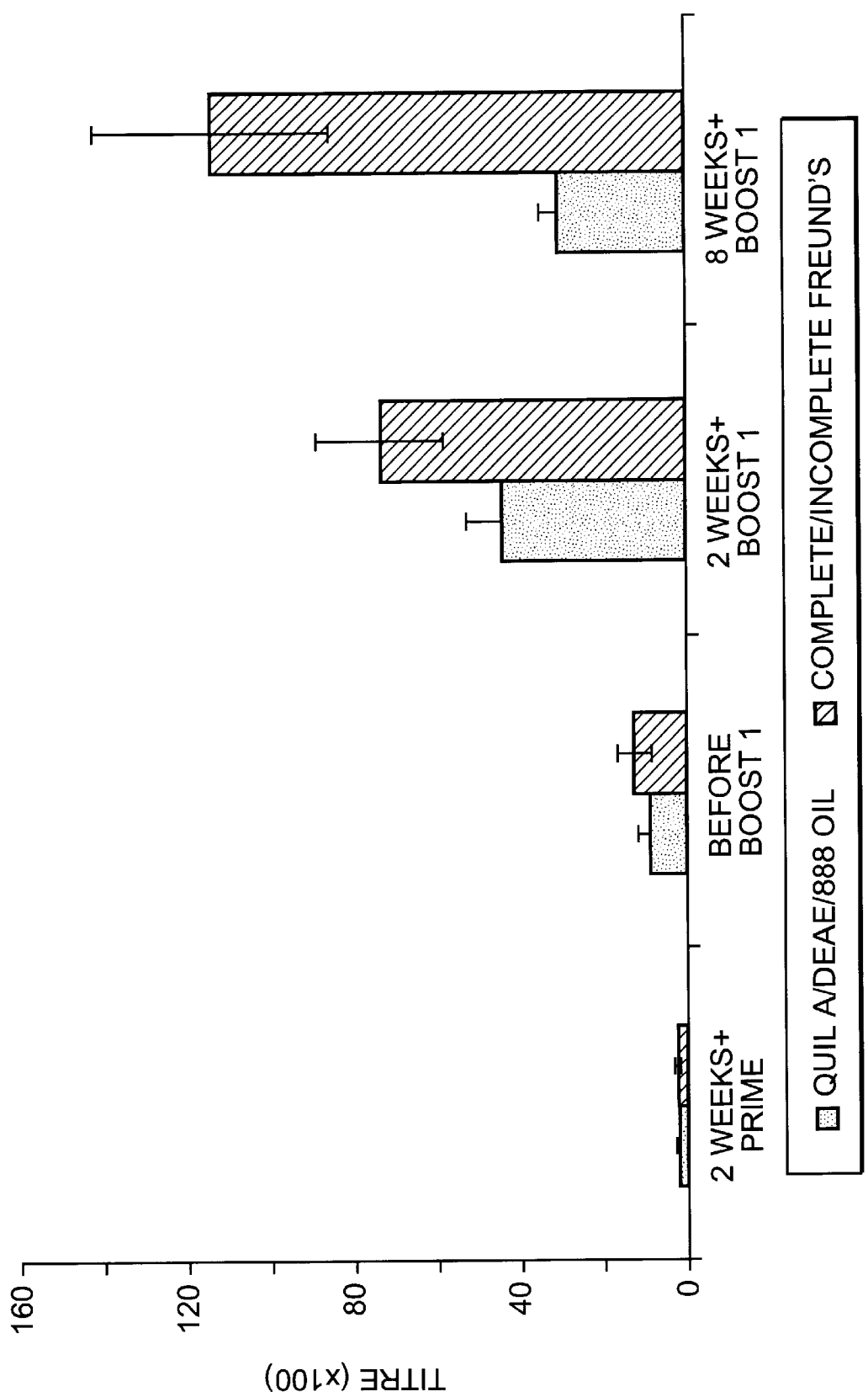

The results obtained are shown in FIGS. 3 and 4 and Tables 8 to 12.

TABLE 8

Adjuvant trial in cattle

| Adjuvant | Animal no. Left | Sex | Animal no. Right | Before prime | Weight (kg) Before boost 1 | Before boost 1 | 8 weeks after boost 1 |
|---|---|---|---|---|---|---|---|
| (Quil A/ | 5 | Female | 373 | 148 | 164 | 186 | 210 | 210 |
| DEAE/ | 6 | Male | 9721 | 183 | 203 | 240 | 282 | 282 |
| 888 oil) | 14 | Male | 9701 | 173 | 188 | 226 | 256 | 256 |
|  | 15 | Male | 9713 | 153 | 171 | 194 | 230 | 230 |
|  | 20 | Female | 998 | 138 | 152 | 169 | 194 | 194 |
|  | 24 | Female | 285 | 156 | 174 | 194 | 221 | 221 |
|  | 25 | Male | 342 | 135 | 152 | 182 | 202 | 202 |
|  | 28 | Female | 9723 | 184 | 200 | 227 | 256 | 256 |
|  | 30 | Female | 9710 | 160 | 180 | 209 | 224 | 224 |
|  | 31 | Male | 9732 | 157 | 176 | 209 | 230 | 230 |
|  | 34 | Male | 631 | 155 | 164 | 177 | 210 | 210 |
|  | 35 | Female | 9720 | 165 | 178 | 183 | 216 | 216 |
|  | 37 | Female | 425 | 176 | 186 | 211 | 241 | 241 |
| Mean |  |  |  | 160 | 176 | 201 | 229 | 229 |
| Counts |  |  |  | 13 | 13 | 13 | 13 | 13 |
| SD |  |  |  | 15 | 16 | 22 | 25 | 25 |
| SE |  |  |  | 4 | 4 | 6 | 7 | 7 |

| Adjuvant | Animal no. Left | Sex | Animal no. Right | Before prime | Weight (kg) Before boost 1 | 8 weeks after boost 1 |
|---|---|---|---|---|---|---|
| CF/ICF | 4 | Male | 9726 | 143 | 148 | 162 | 199 | 199 |
|  | 8 | Female | 9709 | 140 | 150 | 167 | 185 | 185 |
|  | 10 | Female | 9705 | 155 | 168 | 185 | 205 | 205 |
|  | 13 | Male | 979 | 157 | 175 | 187 | 215 | 215 |
|  | 17 | Male | 983 | 183 | 204 | 221 | 252 | 252 |
|  | 19 | Female | 215 | 168 | 193 | 220 | 255 | 255 |
|  | 22 | Female | 377 | 167 | 173 | 169 | 200 | 200 |
|  | 23 | Female | 263 | 146 | 160 | 162 | 206 | 206 |
|  | 26 | Male | 9730 | 176 | 188 | 214 | 232 | 232 |
|  | 32 | Female | 466 | 160 | 178 | 199 | 222 | 222 |
|  | 36 | Male | 418 | 116 | 124 | 143 | 174 | 174 |
| Mean |  |  |  | 155 | 169 | 184 | 213 | 213 |
| Counts |  |  |  | 11 | 11 | 11 | 11 | 11 |
| SD |  |  |  | 19 | 23 | 26 | 26 | 26 |
| SE |  |  |  | 6 | 7 | 8 | 8 | 8 |

TABLE 9

Adjuvant trial in cattle

Tissue reactions to phomopsins-ovalbumin conjugate (2 ml/dose)

| Adjuvant | Animal no. Left | Sex | Animal no. Right | 2 weeks after prime | Before boost 1 | 2 weeks after boost 1 | 8 weeks after boost 1 |
|---|---|---|---|---|---|---|---|
| (Quil A/ | 5 | Female | 373 | | | | |
| DEAE/ | 6 | Male | 9721 | | | 3 × 3 cm | |
| 888 oil) | 14 | Male | 9701 | | | | |
| | 15 | Male | 9713 | | | | |
| | 20 | Female | 998 | | | | |
| | 24 | Female | 285 | | | | |
| | 25 | Male | 342 | | | | |
| | 28 | Female | 9723 | | | 3 × 5 cm | 3 × 4 cm |
| | 30 | Female | 9710 | | | | |
| | 31 | Male | 9732 | 7 × 5 cm | 7 × 5 cm | 4 × 5 cm | 3 × 3 cm |
| | 34 | Male | 631 | | | 3 × 3 cm | |
| | 35 | Female | 9720 | | | | |
| | 37 | Female | 425 | | | | |
| CF/ICF | 4 | Male | 9726 | | | | 3 × 3 cm |
| | 8 | Female | 9709 | 8 × 5 cm | | 6 × 4 cm | 8 × 6 cm |
| | 10 | Female | 9705 | 10 × 3 cm | 6 × 5 cm | | 3 × 4 cm |
| | 13 | Male | 979 | | | | |
| | 17 | Male | 983 | 12 × 6 cm | 8 × 6 cm | 2 × 2 cm | |
| | 19 | Female | 215 | 8 × 5 cm | 4 × 8 cm | 4 × 5 cm | |
| | 22 | Female | 377 | | | | |
| | 23 | Female | 263 | | | 6 × 7 cm | 3 × 3 cm |
| | 26 | Male | 9730 | | 7 × 5 cm | | |
| | 32 | Female | 466 | | | 8 × 8 cm | 4 × 5 cm |
| | 36 | Male | 418 | 10 × 6 cm | | 7 × 8 cm | 7 × 6 cm |

TABLE 10

Adjuvant trial in cattle

Tissue reactions to 5 in 1 vaccine (4 ml/dose)

| Adjuvant | Animal no. Left | Sex | Animal no. Right | 4 weeks after prime | Before boost 1 | 2 weeks after boost 1 | 8 weeks after boost 1 |
|---|---|---|---|---|---|---|---|
| (Quil A/ | 5 | Female | 373 | | | | |
| DEAE/ | 6 | Male | 9721 | | | | |
| 888 oil) | 14 | Male | 9701 | | | | |
| | 15 | Male | 9713 | | 2 × 2 cm | 2 × 3 cm | 3 × 5 cm |
| | 20 | Female | 998 | 4 × 3 cm | 4 × 4 cm | 1 × 1 cm | |
| | 24 | Female | 285 | | | | |
| | 25 | Male | 342 | | 2 × 2 cm | 8 × 5 cm | 5 × 5 cm |
| | 28 | Female | 9723 | | | | |
| | 30 | Female | 9710 | | | 5 × 4 cm | 5 × 6 cm |
| | 31 | Male | 9732 | | | 5 × 5 cm | 3 × 4 cm |
| | 34 | Male | 631 | | 4 × 4 cm | 3 × 3 cm | |
| | 35 | Female | 9720 | 3 × 2 cm | 3 × 2 cm | 7 × 5 cm | |
| | 37 | Female | 425 | 4 × 2 cm | 3 × 3 cm | | |
| CF/ICF | 4 | Male | 9726 | 2 × 2 cm | | 6 × 3 cm | 3 × 3 cm |
| | 8 | Female | 9709 | | 2 × 2 cm | 1 × 1 cm | |
| | 10 | Female | 9705 | | | 6 × 4 cm | 3 × 5 cm |
| | 13 | Male | 979 | | | 7 × 6 cm | |
| | 17 | Male | 983 | 5 × 3 cm | 5 × 5 cm | 3 × 4 + 10 × 10 cm | |
| | 19 | Female | 215 | | | | |
| | 22 | Female | 377 | | | 3 × 3 cm | |
| | 23 | Female | 263 | 5 × 4 cm | | 3 × 3 cm | |
| | 26 | Male | 9730 | 3 × 2 cm | | 3 × 4 cm | 3 × 3 cm |
| | 32 | Female | 466 | | | | |
| | 36 | Male | 418 | | | 3 × 5 cm | |

TABLE 11

Adjuvant trial in cattle

Anti-phomopsin IgG titre (× 100)

| Adjuvant | Animal No. | Sex | 2 weeks after prime | Before boost 1 | 2 weeks after boost 1 | 8 weeks after boost 1 |
|---|---|---|---|---|---|---|
| (Quil A/ | 5 | Female | 16 | 38 | 120 | 95 |
| DEAE/ | 6 | Male | 7 | 17 | 134 | 60 |
| 888 oil) | 14 | Male | 26 | 170 | 514 | 158 |
| | 15 | Male | 12 | 20 | 99 | 51 |
| | 20 | Female | 4 | 22 | 119 | 74 |
| | 24 | Female | 17 | 121 | 286 | 92 |
| | 25 | Male | 11 | 17 | 50 | 24 |
| | 28 | Female | 26 | 162 | 340 | 116 |
| | 30 | Female | 16 | 33 | 86 | 46 |
| | 31 | Male | 29 | 81 | 261 | 156 |
| | 34 | Male | 5 | 23 | 94 | 59 |
| | 35 | Female | 14 | 74 | 200 | 191 |
| | 37 | Female | 8 | 50 | 237 | 231 |
| Mean | | | 15 | 64 | 195 | 104 |
| Counts | | | 13 | 13 | 13 | 13 |
| SD | | | 8 | 55 | 131 | 63 |
| SE | | | 2 | 15 | 36 | 17 |
| CF/ICF | 4 | Male | 7 | 17 | 60 | 129 |
| | 8 | Female | 12 | 64 | 291 | 299 |
| | 10 | Female | 2 | 27 | 186 | 173 |
| | 13 | Male | 10 | 45 | 186 | 93 |
| | 17 | Male | 8 | 74 | 299 | 142 |
| | 19 | Female | 5 | 19 | 162 | 28 |
| | 22 | Female | 11 | 104 | 595 | 128 |
| | 23 | Female | 4 | 45 | 205 | 128 |
| | 26 | Male | 9 | 41 | 256 | 302 |
| | 32 | Female | 10 | 70 | 231 | 240 |
| | 36 | Male | 3 | 19 | 94 | 82 |
| Mean | | | 7 | 48 | 233 | 158 |
| Counts | | | 11 | 11 | 11 | 11 |
| SD | | | 3 | 28 | 141 | 88 |
| SE | | | 1 | 8 | 43 | 27 |

TABLE 12

Adjuvant trial in cattle

Anti-ovalbumin IgG titre (× 100)

| Adjuvant | Animal No. | Sex | 2 weeks after prime | Before boost 1 | 2 weeks after boost 1 | 8 weeks after boost 1 |
|---|---|---|---|---|---|---|
| (Quil A/ | 5 | Female | 4 | 5 | 8 | 15 |
| DEAE/ | 6 | Male | 6 | 8 | 78 | 43 |
| 888 oil) | 14 | Male | 2 | 40 | 110 | 63 |
| | 15 | Male | 2 | 3 | 13 | 28 |
| | 20 | Female | 2 | 9 | 77 | 36 |
| | 24 | Female | 3 | 9 | 78 | 22 |
| | 25 | Male | 2 | 3 | 37 | 35 |
| | 28 | Female | 1 | 19 | 35 | 43 |
| | 30 | Female | 5 | 5 | 32 | 24 |
| | 31 | Male | 2 | 5 | 29 | 15 |
| | 34 | Male | 1 | 2 | 9 | 6 |
| | 35 | Female | 0 | 4 | 25 | 51 |
| | 37 | Female | 2 | 4 | 49 | 19 |
| Mean | | | 2 | 9 | 45 | 31 |
| Counts | | | 13 | 13 | 13 | 13 |
| SD | | | 2 | 10 | 32 | 16 |
| SE | | | 0 | 3 | 9 | 4 |
| CF/ICF | 4 | Male | 2 | 3 | 10 | 29 |
| | 8 | Female | 2 | 23 | 84 | 113 |
| | 10 | Female | 1 | 6 | 19 | 16 |
| | 13 | Male | 2 | 4 | 60 | 37 |
| | 17 | Male | 4 | 15 | 147 | 181 |
| | 19 | Female | 2 | 5 | 51 | 34 |
| | 22 | Female | 3 | 15 | 63 | 73 |
| | 23 | Female | 1 | 15 | 85 | 237 |
| | 26 | Male | 2 | 6 | 52 | 173 |
| | 32 | Female | 5 | 42 | 178 | 285 |

TABLE 12-continued

Adjuvant trial in cattle

Anti-ovalbumin IgG titre (x 100)

| Adjuvant | Animal No. | Sex | 2 weeks after prime | Before boost 1 | 2 weeks after boost 1 | 8 weeks after boost 1 |
|---|---|---|---|---|---|---|
| | 36 | Male | 2 | 8 | 70 | 77 |
| Mean | | | 3 | 13 | 75 | 114 |
| Counts | | | 11 | 11 | 11 | 11 |
| SD | | | 1 | 12 | 50 | 92 |
| SE | | | 0 | 3 | 15 | 28 |

EXAMPLE 7

In this example a comparison was made between sheep injected with a phomopsin A fetal calf serum conjugate in Freund's complete adjuvant with a booster injection given in incomplete Freund's adjuvant and the same antigen injected in an adjuvant formulation prepared according to this invention.

Primary injections were started during marking of 10 to 12 weeks old lambs. Twenty four, ten to twelve weeks old lambs, weighing between 10 to 20 kg, were weighed and 10 ml blood was collected from jugular vein. They were divided into two equal groups randomised according to weight. One group was injected with 50 µg phomopsin A conjugated to 220 µg foetal calf serum, 0.5 mg Quil A and 5 mg DEAE-dextran dissolved in 0.8 ml of sterile water and emulsified with 1.2 ml of Montanide 888 oil (60%). The second group was injected with phomopsin A 50 µg conjugated to foetal calf serum 220 µg dissolved in 1 ml of sterile water, and emulsified with 1 ml of Complete Freund's adjuvant. Both groups were injected subcutaneously with 2 ml to the right side of the back of the neck, below the ear. In addition all lambs received an injection of 2 ml of six in one plus selenium vaccine, injected subcutaneously at a separate site.

Two weeks after the primary injection lambs were weighed, tissue reactions at the injection sites were inspected and 10 ml blood was collected from jugular vein. A second dose of six in one plus selenium vaccine was injected subcutaneously at the back of the neck behind the ear.

Three months after the primary injection lambs were weighed, tissue reactions at the injection sites were inspected and 10 ml blood was collected from jugular vein. A booster injection of phomopsin A 50 µg conjugated to 220 µg foetal calf serum was given subcutaneously as in primary injection. In the case of the comparison group Incomplete Fruendis Adjuvant was used as the adjuvant in place of Freunds complete adjuvant.

Two weeks after the booster injection lambs were weighed, tissue reactions at the injection sites were inspected and 10 ml blood was collected from jugular vein.

Eight weeks after the booster injection lambs were weighed and tissue reactions at the injection sites were inspected and 10 ml blood was collected from jugular vein.

ELISA on 50 ng Phomopsins/well Coated Microtitre Plates

Phomopsins were diluted as 50 ng/100 µl in carbonate coating buffer pH 9.6 and 100 µl of the solution was added microtitre plates (sarstedt, Australia). After overnight incubation at 40° C., the plates were washed four times with 0.05 tween 20 in saline. After the washing, 100 µl of 0.1% gelatine in phosphate buffered saline was added to all wells of microtiter plates. Reference serum and sera for testing, diluted 1/100 in 0.1% gelatine in phosphate buffered saline, were then added to the wells of row 2. Two fold serial dilutions were performed across the plates. After 2 hours incubation at room temperature, the plates were washed four times and 100 µl of 1/14,000 anti-sheep IgG, developed in donkey, conjugated to peroxidase (Sigma Cat. A 3415) was added and incubated for a further 2 hour. After washing the plate four times 3, 3', 5, 5'-tetramethylbenzidine (Sigma Cat. T2885) substrate was added and incubated for a further 20 minutes before the stopping solution was added. Titres were expressed as the reciprocal of the dilution resulting in 0.5 optical density of the wells.

ELISA on 50 ng foetal calf serum/well coated microtitre plates

ELISA was also performed on 50 ng foetal calf serum/well coated plates as above in phomopsins 50 ng/well coated plates except 96 wells, flat bottom, Nunc-Immuno polysorp microtitre plates (Cat. 475094) were used and coating was done at 4° C.

Figure 5:
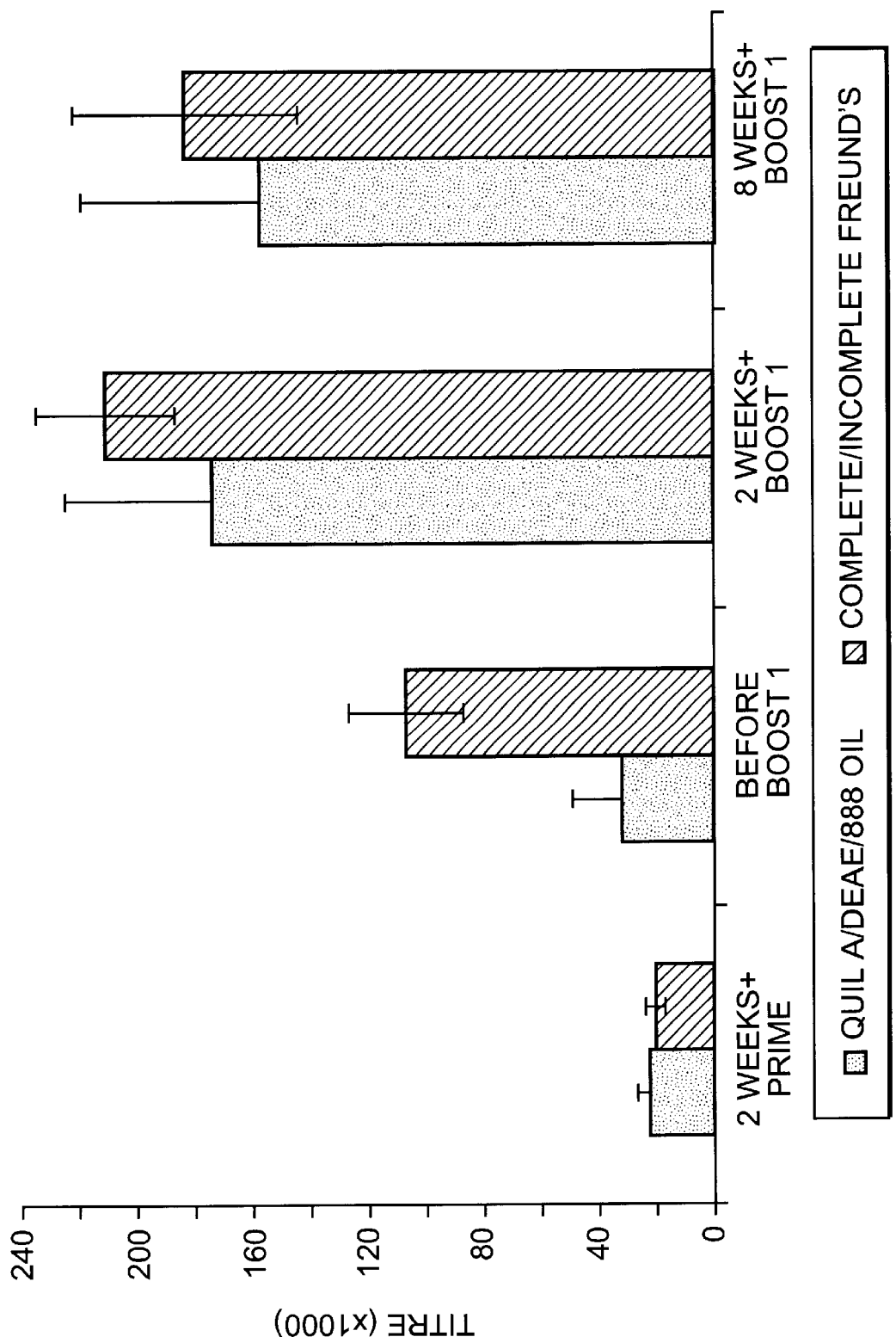
Figure 6:
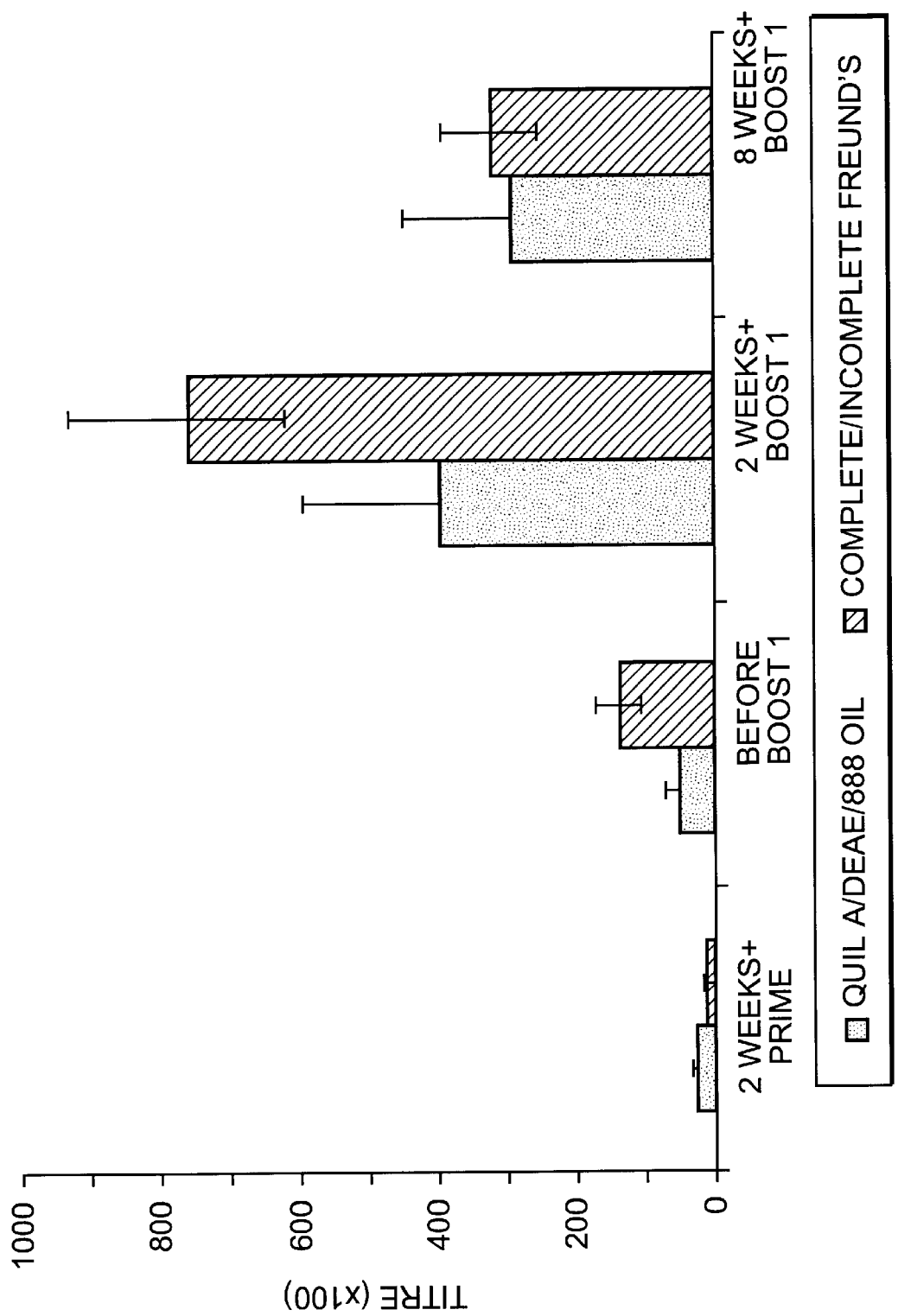

The results obtained are shown in FIGS. 5 and 6 and

Tables 13 to 15.

TABLE 13

Adjuvant trial in wethers

| | | Weight (kg) | | | | |
|---|---|---|---|---|---|---|
| Adjuvant | Animal no. | Before prime | 2 weeks after prime | Before boost 1 | 2 weeks after boost 1 | 8 weeks after boost 1 |
| (Quil A/ | 85 | 11.5 | 18.7 | 28.6 | 31.0 | 28.0 |
| DEAE/ | 86 | 14.0 | 18.3 | 28.4 | 30.0 | 26.5 |
| 888 oil) | 87 | 15.5 | 20.2 | 20.2 | 19.0 | 15.5 |
| | 88 | 14.5 | 21.4 | 32.4 | 35.5 | 29.5 |

TABLE 13-continued

Adjuvant trial in wethers

|  |  |  |  |  |  |  |
|---|---|---|---|---|---|---|
|  | 89 | 14.5 | 19.1 | 32.0 | 33.5 | 30.5 |
|  | 90 | 16.5 | 22.6 | 23.8 | 33.5 | 29.5 |
|  | 91 | 15.0 | 20.2 | 31.0 | 30.0 | 24.0 |
|  | 92 | 11.5 | 16.1 | 24.0 | 26.5 | 23.0 |
|  | 93 | 16.0 | 21.6 | 30.6 | 33.0 | 30.0 |
|  | 94 | 12.5 | 19.6 | 28.2 | 31.0 | 26.5 |
|  | 95 | 13.0 | 19.5 | 26.4 | 28.0 | 23.5 |
|  | 96 | 13.5 | 20.2 | 34.2 | 37.5 | 34.5 |
| Mean |  | 14.0 | 19.8 | 28.3 | 30.7 | 26.8 |
| SD |  | 1.65 | 1.70 | 4.11 | 4.80 | 4.86 |
| Counts |  | 12 | 12 | 12 | 12 | 12 |
| SE |  | 0.48 | 0.49 | 1.19 | 1.39 | 1.40 |

| Adjuvant | Animal no. Left | Weight (kg) ||||
|---|---|---|---|---|---|
|  |  | Before prime | 2 weeks after prime | Before boost 1 | 2 weeks after boost 1 | 8 weeks after boost 1 |
| CF/ICF | 145 | 15.0 | 20.4 | 29.8 | 34.0 | 31.5 |
|  | 146 | 13.0 | 18.2 | 28.6 | 32.5 | 29.5 |
|  | 147 | 10.5 | 13.5 | 15.6 | 17.0 | 12.5 |
|  | 148 | 12.5 | 16.3 | 27.2 | 30.0 | 27.0 |
|  | 149 | 16.0 | 21.4 | 32.4 | 35.5 | 30.5 |
|  | 150 | 17.5 | 22.0 | 36.2 | 36.0 | 31.0 |
|  | 151 | 13.5 | 17.3 | 26.2 | 28.0 | 24.5 |
|  | 152 | 18.0 | 24.2 | 37.2 | 38.5 | 34.5 |
|  | 153 | 17.5 | 22.4 | 31.2 | 30.5 | 28.0 |
|  | 154 | 16.0 | 20.4 | 27.4 | 30.0 | 25.0 |
|  | 155 | 15.5 | 19.5 | 32.2 | 35.0 | 31.0 |
|  | 156 | 14.0 | 19.7 | 25.2 | 27.5 | 25.0 |
| Mean |  | 14.9 | 19.6 | 29.1 | 31.2 | 27.5 |
| SD |  | 2.28 | 2.93 | 5.67 | 5.62 | 5.64 |
| Counts |  | 12 | 12 | 12 | 12 | 12 |
| SE |  | 0.66 | 0.85 | 1.64 | 1.62 | 1.63 |

By eight weeks after boost 1 all sheep lost body weight due to the drought and lack of food.

TABLE 14

Adjuvant trial in wethers

Anti-phomopsin IgG titre (×1000)

| Adjuvant | Animal No. | 2 weeks after prime | Before boost 1 | 2 weeks after boost 1 | 8 weeks after boost 1 |
|---|---|---|---|---|---|
| (Quil A/ | 85 | 21 | 5 | 95 | 57 |
| DEAE/ | 86 | 14 | 22 | 281 | 145 |
| 888 oil) | 87 | 26 | 7 | 68 | 33 |
|  | 88 | 20 | 10 | 59 | 72 |
|  | 89 | 50 | 215 | 328 | 565 |
|  | 90 | 31 | 15 | 165 | 71 |
|  | 91 | 37 | 40 | 662 | 640 |
|  | 92 | 28 | 9 | 75 | 56 |
|  | 93 | 19 | 10 | 92 | 54 |
|  | 94 | 8 | 27 | 61 | 86 |
|  | 95 | 15 | 8 | 84 | 56 |
|  | 96 | 7 | 24 | 98 | 62 |
| Mean |  | 23 | 33 | 172 | 158 |
| Counts |  | 12 | 12 | 12 | 12 |
| SD |  | 12 | 58 | 178 | 210 |
| SE |  | 4 | 17 | 51 | 61 |
| CF/ICF | 145 | 9 | 49 | 211 | 62 |
|  | 146 | 11 | 50 | 120 | 51 |
|  | 147 | 21 | 144 | 274 | 219 |
|  | 148 | 14 | 51 | 105 | 83 |
|  | 149 | 22 | 219 | 256 | 140 |
|  | 150 | 45 | 203 | 298 | 351 |
|  | 151 | 15 | 48 | 121 | 80 |
|  | 152 | 36 | 107 | 365 | 494 |
|  | 153 | 22 | 56 | 151 | 191 |
|  | 154 | 20 | 188 | 197 | 165 |
|  | 155 | 22 | 49 | 252 | 109 |

TABLE 14-continued

Adjuvant trial in wethers

Anti-phomopsin IgG titre (×1000)

| Adjuvant | Animal No. | 2 weeks after prime | Before boost 1 | 2 weeks after boost 1 | 8 weeks after boost 1 |
|---|---|---|---|---|---|
|  | 156 | 11 | 134 | 173 | 252 |
| Mean |  | 21 | 108 | 210 | 183 |
| Counts |  | 12 | 12 | 12 | 12 |
| SD |  | 11 | 67 | 81 | 132 |
| SE |  | 3 | 19 | 23 | 38 |

TABLE 15

Adjuvant trial in wethers

Anti-foetal calf serum IgG titre (×100)

| Adjuvant | Animal No. | 2 weeks after prime | Before boost 1 | 2 weeks after boost 1 | 8 weeks after boost 1 |
|---|---|---|---|---|---|
| (Quil A/ | 85 | 6 | 7 | 120 | 127 |
| DEAE/ | 86 | 17 | 41 | 403 | 176 |
| 888 oil) | 87 | 20 | 15 | 148 | 53 |
|  | 88 | 13 | 25 | 132 | 123 |
|  | 89 | 71 | 238 | 656 | 343 |
|  | 90 | 14 | 24 | 125 | 68 |
|  | 91 | 39 | 47 | 2290 | 1915 |
|  | 92 | 10 | 15 | 116 | 65 |
|  | 93 | 24 | 26 | 135 | 141 |
|  | 94 | 25 | 58 | 164 | 207 |
|  | 95 | 10 | 41 | 288 | 230 |
|  | 96 | 20 | 67 | 228 | 131 |

TABLE 15-continued

Adjuvant trial in wethers

Anti-foetal calf serum IgG titre (×100)

| Adjuvant | Animal No. | 2 weeks after prime | Before boost 1 | 2 weeks after boost 1 | 8 weeks after boost 1 |
|---|---|---|---|---|---|
| Mean |  | 22 | 50 | 400 | 298 |
| Counts |  | 12 | 12 | 12 | 12 |
| SD |  | 18 | 62 | 616 | 516 |
| SE |  | 5 | 18 | 178 | 149 |
| CF/ICF | 145 | 6 | 23 | 246 | 130 |
|  | 146 | 4 | 42 | 173 | 59 |
|  | 147 | 9 | 143 | 395 | 164 |
|  | 148 | 4 | 29 | 156 | 45 |
|  | 149 | 15 | 332 | 1453 | 195 |
|  | 150 | 15 | 77 | 1015 | 317 |
|  | 151 | 32 | 277 | 990 | 806 |
|  | 152 | 9 | 141 | 855 | 636 |
|  | 153 | 12 | 97 | 676 | 473 |
|  | 154 | 22 | 289 | 1837 | 496 |
|  | 155 | 7 | 84 | 301 | 173 |
|  | 156 | 9 | 97 | 994 | 382 |
| Mean |  | 12 | 136 | 758 | 323 |
| Counts |  | 12 | 12 | 12 | 12 |
| SD |  | 8 | 106 | 535 | 240 |
| SE |  | 2 | 31 | 154 | 69 |

EXAMPLE 8

In this example the immunogen was ovalbumin. It was injected into rats in complete Freund's adjuvant for the primary injection and incomplete Freund's for a booster injection. The antibody response obtained was compared with that of sheep given the same antigen formulated in an adjuvant prepared according to this invention.

Female Long-Evans hooded rats were kept in cages of 4 rats/cage. Twenty five, twelve weeks old Long-Evans rats were weighed and divided into two groups. 0.2 to 0.5 ml blood was collected from tail vein prior to vaccination. For the primary injection using an adjuvant formulation typical of this invention, 65 µg ovalbumin, 40 µg Quil A and 0.8 mg DEAE-dextran were dissolved in 0.128 ml of phosphate buffered saline and emulsified with 0.192 ml of Montanide 888 oil (60%). In the comparison group 65 µg ovalbumin was dissolved in 0.16 ml of phosphate buffered saline and emulsified with 0.16 ml of Complete Freund's adjuvant (50%). Both groups were injected subcutaneously as a total volume of 0.32 ml divided into two sites at the back.

Two weeks after the primary injection the rats were weighed, tissue reactions at the injection sites were inspected and 0.2 to 0.5 ml blood was collected from tail vein.

Twelve days later the rats were re-weighed, tissue reactions at the injection sites were inspected and 0.2 to 0.5 ml blood was collected from tail vein. For the booster injection, 65 µg ovalbumin was given subcutaneously as in primary injection. Incomplete Freund's Adjuvant was used in place of complete Freund's adjuvant for the comparison group.

One week after the booster injection and then again two weeks after the booster injection the rats were weighed again, tissue reactions at the injection sites were inspected and 0.2 to 0.5 ml blood was collected from tail vein.

Four weeks after the booster injection the rats were weighed and tissue reactions at the injection sites were inspected.

Eight weeks after the booster injection the rats were weighed, tissue reactions at the injection sites were inspected and 0.2 to 0.5 ml blood was collected from tail vein.

ELISA on 50 ng Ovalbumin/well Coated Mlicrotitre Plates

Ovalbumin was diluted as 50 ng/0.1 ml in carbonate coating buffer pH 9.6 and 100 µl of the solution was added to all wells of row 2 to 12 of 96 wells, flat bottom, microtitre plates (Nunc-Immuno plate, F 96 Cert.maxisorp, Cat. 439454). After overnight incubation at 4° C., the plates were washed four times with 0.05% tween 20 in saline. After the washing, 100 µl of 0.1% gelatine in phosphate buffered saline was added to all wells of microtiter plates. This was followed by the addition of the reference serum and sera for testing, diluted 1/100 in 0.1% gelatine in phosphate buffered saline, to the wells of row 2. Two fold serial dilutions were performed across the plates. After 2 hours incubation at room temperature, the plates were washed four times and 100 µl of 1/16,000 anti-rat IgG, developed in goat, conjugated to peroxidase (Sigma Cat. A 9037) was added and incubated for a further 2 hours. After washing the plate four times 3, 3', 5, 5'-tetramethylbenzidine (Sigma Cat. T2885) substrate was added and incubated for a further 20 minutes before the stopping solution was added. Titres were expressed as the reciprocal of the dilution resulting in 0.5 optical density of the wells.

Figure 7:
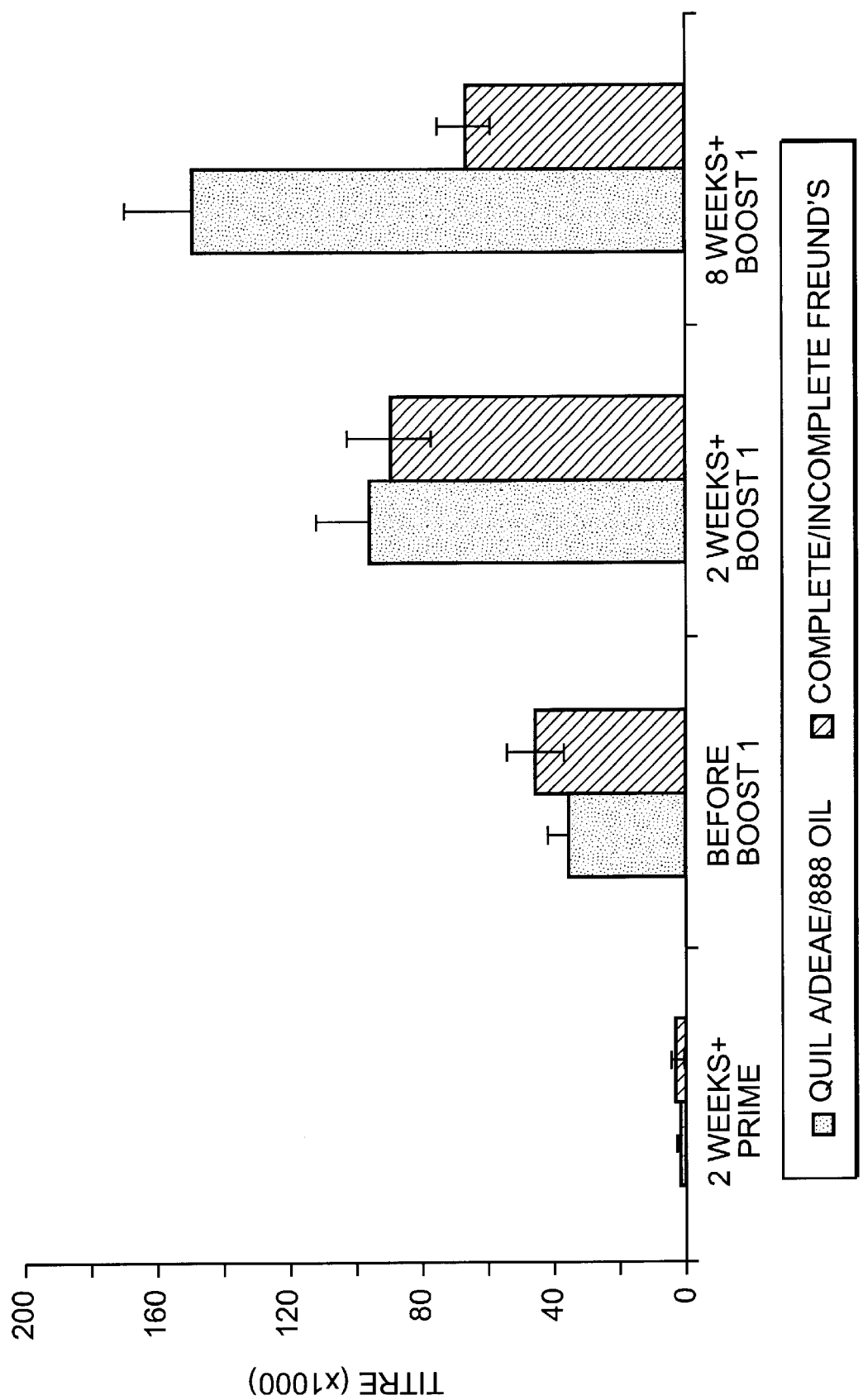

The results are shown in FIG. 7 and Tables 16 to 18.

TABLE 16

Adjuvant trial in Long-Evans female rats

Body weight (gm)

| Adjuvant | Cage/ Animal No. | Before prime | 2 weeks after prime | Before boost 1 | 1 week after boost 1 | 2 weeks after boost 1 | 4 weeks after boost 1 | 8 weeks after boost 1 |
|---|---|---|---|---|---|---|---|---|
| (Quil A/ | Cage 1/0 | 197 | 208 | 212 | 214 | 219 | 224 | 222 |
| DEAE/ | Cage 1/1 | 199 | 212 | 220 | 210 | 237 | 234 | 230 |
| 888 oil) | Cage 1/2 | 182 | 189 | 196 | 192 | 198 | 202 | 204 |
|  | Cage 1/3 | 203 | 201 | 208 | 216 | 234 | 217 | 222 |
|  | Cage 2/0 | 192 | 207 | 217 | 215 | 220 | 203 | 232 |
|  | Cage 2/1 | 207 | 222 | 226 | 221 | 228 | 229 | 233 |
|  | Cage 2/2 | 202 | 211 | 214 | 215 | 222 | 225 | 226 |
|  | Cage 2/3 | 234 | 224 | 230 | 231 | 234 | 241 | 247 |

TABLE 16-continued

Adjuvant trial in Long-Evans female rats

| Adjuvant | Cage/ Animal No. | Before prime | 2 weeks after prime | Before boost 1 | 1 week after boost 1 | 2 weeks after boost 1 | 4 weeks after boost 1 | 8 weeks after boost 1 |
|---|---|---|---|---|---|---|---|---|
| | Cage 3/1 | 189 | 170 | 198 | 219 | 232 | 215 | 211 |
| | Cage 3/2 | 205 | 190 | 230 | 240 | 233 | 221 | 234 |
| | Cage 3/3 | 198 | 184 | 207 | 211 | 213 | 238 | 234 |
| | Cage 7/1 | 223 | 224 | 223 | 233 | 234 | 232 | 235 |
| | Cage 7/2 | 228 | 229 | 227 | 238 | 238 | 235 | 235 |
| Mean | | 205 | 205 | 216 | 220 | 226 | 224 | 228 |
| Counts | | 13 | 13 | 13 | 13 | 13 | 13 | 13 |
| SD | | 15 | 18 | 11 | 13 | 12 | 12 | 11 |
| SE | | 4 | 5 | 3 | 4 | 3 | 3 | 3 |
| CF/ICF | Cage 4/0 | 205 | 214 | 219 | 222 | 222 | 231 | 246 |
| | Cage 4/1 | 186 | 198 | 209 | 204 | 207 | 221 | 222 |
| | Cage 4/2 | 198 | 207 | 206 | 206 | 210 | 220 | 225 |
| | Cage 4/3 | 200 | 211 | 230 | 224 | 227 | 233 | 236 |
| | Cage 5/0 | 198 | 216 | 220 | 222 | 232 | 233 | 235 |
| | Cage 5/1 | 194 | 208 | 210 | 206 | 218 | 229 | 221 |
| | Cage 5/2 | 196 | 206 | 213 | 215 | 222 | 226 | 230 |
| | Cage 5/3 | 205 | 213 | 218 | 224 | 234 | 237 | 241 |
| | Cage 6/0 | 191 | 204 | 221 | 218 | 221 | 225 | 253 |
| | Cage 6/1 | 207 | 223 | 254 | 233 | 236 | 235 | 240 |
| | Cage 6/2 | 215 | 234 | 241 | 236 | 241 | 240 | 248 |
| | Cage 6/3 | 182 | 203 | 212 | 208 | 210 | 210 | 212 |
| Mean | | 198 | 211 | 221 | 218 | 223 | 228 | 234 |
| Counts | | 12 | 12 | 12 | 12 | 12 | 12 | 12 |
| SD | | 9 | 10 | 14 | 11 | 11 | 8 | 12 |
| SE | | 3 | 3 | 4 | 3 | 3 | 2 | 4 |

TABLE 17

Adjuvant trial in Long-Evans female rats

| Adjuvant | Cage/ Animal No. | 5 days after prime | 11 days after prime | 1 week after boost 1 | 2 weeks after boost 1 | 8 weeks after boost 1 |
|---|---|---|---|---|---|---|
| (Quil A/ DEAE/ 888 oil) | Cage 1/0 | | | | | |
| | Cage 1/1 | | | | | 1+ |
| | Cage 1/2 | | | | | 1+ |
| | Cage 1/3 | | | | 1++ | 1+ |
| | Cage 2/0 | | | | | 1+ |
| | Cage 2/1 | | | | | |
| | Cage 2/2 | 1++ | 1++ | | | 1+ |
| | Cage 2/3 | | | | | 1+ |
| | Cage 3/1 | | | | | |
| | Cage 3/2 | | | | | 1+ |
| | Cage 3/3 | | | | | |
| | Cage 7/1 | | | | | |
| | Cage 7/2 | | | | | |
| CF/ICF | Cage 4/0 | 1++ | 1++ | | 1+ | 2++ |
| | Cage 4/1 | 1+ | 1+ | | 1+++ | 2++ |
| | Cage 4/2 | 1++ | 1++ | | 1++ | 2++ |
| | Cage 4/3 | 1+ | 1+ | | 2++ | 2++ |
| | Cage 5/0 | 1++ | 1++ | | 2++ | 2++ |
| | Cage 5/1 | 2++ | 2++ | | 2+ | 1+, 1++ |
| | Cage 5/2 | 1+ | 1+ | | 1+, 1+++ | 1+, 1++ |
| | Cage 5/3 | | 1+ | | | 1+, 1+++ |
| | Cage 6/0 | 1+++opened | 1++ | 2+ | 2+ | 1+, 1++ |
| | Cage 6/1 | 1++opened | 1++ | 1+++opened | 1+++ | 2+ |
| | Cage 6/2 | | 1+ | 1+++ | 1+, 1+++ | 1+, 1+++ |
| | Cage 6/3 | 1++ | 1++ | | 2++ | 2++ |

+ = small lump (1–2 mm)
++ = Medium lump (3–5 mm)
+++ = Big lump (more than 5 mm)
1 and 2 = numbers of lumps

TABLE 18

Adjuvant trial in Long-Evans female rats

| Adjuvant | Cage/ Animal No. | Titre (×1000) | | | |
|---|---|---|---|---|---|
| | | 2 weeks after prime | Before boost 1 | 2 weeks after boost 1 | 8 weeks after boost 1 |
| (Quil A/ | Cage 1/0 | 1 | 33 | 155 | 247 |
| DEAE/ | Cage 1/1 | 1 | 38 | 68 | 156 |
| 888 oil) | Cage 1/2 | 1 | 13 | 28 | 96 |
| | Cage 1/3 | 0 | 9 | 29 | 77 |
| | Cage 2/0 | 1 | 36 | 93 | 126 |
| | Cage 2/1 | 1 | 26 | 85 | 92 |
| | Cage 2/2 | 0 | 12 | 23 | 49 |
| | Cage 2/3 | 0 | 33 | 78 | 173 |
| | Cage 3/1 | 2 | 55 | 155 | 68 |
| | Cage 3/2 | 0 | 28 | 68 | 195 |
| | Cage 3/3 | 10 | 91 | 164 | 246 |
| | Cage 7/1 | 1 | 57 | 210 | 252 |
| | Cage 7/2 | 0 | 21 | 80 | 150 |
| Mean | | 1 | 35 | 95 | 148 |
| Counts | | 13 | 13 | 13 | 13 |
| SD | | 3 | 22 | 59 | 71 |
| SE | | 1 | 6 | 16 | 20 |
| CF/ICF | Cage 4/0 | 0 | 18 | 94 | 57 |
| | Cage 4/1 | 0 | 12 | 38 | 33 |
| | Cage 4/2 | 4 | 63 | 120 | 81 |
| | Cage 4/3 | 4 | 67 | 98 | 66 |
| | Cage 5/0 | 2 | 39 | 113 | 69 |
| | Cage 5/1 | 2 | 46 | 67 | 65 |
| | Cage 5/2 | 1 | 2 | 27 | 34 |
| | Cage 5/3 | 2 | 68 | 87 | 55 |
| | Cage 6/0 | 11 | 89 | 174 | 128 |
| | Cage 6/1 | 0 | 62 | 126 | 87 |
| | Cage 6/2 | 4 | 7 | 27 | 36 |
| | Cage 6/3 | 3 | 66 | 95 | 87 |
| Mean | | 3 | 45 | 89 | 67 |
| Counts | | 12 | 12 | 12 | 12 |
| SD | | 3 | 29 | 44 | 27 |
| SE | | 1 | 8 | 13 | 8 |

Examples 5 to 8 demonstrate that the newly invented adjuvant stimulates the immune system of a variety of animal species against a range of antigens with an efficacy similar to or better than the benchmark Freund's adjuvant but without the injection site reactions induced by the latter.

INDUSTRIAL APPLICABILITY

The adjuvant compositions of the present invention are applicable to the preparation of vaccines against a wide range of infectious diseases and against natural products of the human and animal body such as hormones.

What is claimed is:

1. An adjuvant composition for stimulating an effective immune response to an antigenic substance when co-administered to an animal with said antigenic substance, comprising:
   (a) a saponin with immune stimulating activity;
   (b) a polycationic polyelectrolyte with immmue stimulating activity; and
   (c) an immunoadjuvant oil.

2. The adjuvant composition as claimed in claim 1, wherein the saponin is a triterpenoid compound or a mixture of triterpenoid compounds.

3. The adjuvant composition as claimed in claim 2, wherein the saponin is Quil A.

4. The adjuvant composition as claimed in any one of claims 1 to 3, wherein the polycationic polyelectrolyte is diethylaminoethyl dextran.

5. The adjuvant composition as claimed in claim 1, wherein the immunoadjuvant oil is a mineral oil.

6. The adjuvant composition as claimed in claim 1, wherein the mineral oil is Freund's incomplete adjuvant or Montanide oil.

7. A vaccine for administration to an animal, comprising:
   (1) an antigenic substance; and
   (2) an adjuvant composition comprising:
      (a) a saponin with immune stimulating activity;
      (b) a polycationic polyelectrolyte with immne stimulating activity;
      (c) an immunoadjuvant oil.

8. The vaccine as claimed in claim 7, wherein the saponin is a triterpenoid compound or a mixture of triterpenoid compounds.

9. The vaccine as claimed in claim 8, wherein the saponin is a Quil A.

10. The vaccine as claimed in any one of claims 7 to 9, wherein the polycationic polyelectrolyte is diethylaminoethyl dextran.

11. The vaccine as claimed in any one of claims 7 to 9, wherein the immunoadjuvant oil is a mineral oil.

12. The vaccine as claimed in claim 11, wherein the mineral oil is Freund's incomplete adjuvant or a Montanide oil.

13. The vaccine according to claim 7, wherein the saponin is present in a concentration of in between 50 $\mu$g/ml and 10 mg/ml.

14. The vaccine according to claim 13 wherein the saponin is present in a concentration between 100 $\mu$g/ml and 10 mg/ml.

15. The vaccine as claimed in any one of claims 7 to 9, wherein the polycationic polyelectrolyte is present in a concentration between 1 mg/ml and 200 mg/ml.

16. The vaccine as claimed in claim 15 wherein the polycationic polyelectrolyte is present in a concentration between 1.5 mg/ml and 150 mg/ml.

17. A method of stimulating an effective immune response in an animal to an antigenic substance, comprising the steps of:
   (1) providing said antigenic substance;
   (2) providing an adjuvant composition comprising:
      (a) a saponin with immune stimulating activity;
      (b) a polycationic polyelectrolyte with immune stimulating activity; and
      (c) an immunoadjuvant oil; and
   (3) challenging said animal with said antigenic substance and said adjuvant composition.

* * * * *